(12) United States Patent
Stanley

(10) Patent No.: US 8,557,070 B2
(45) Date of Patent: Oct. 15, 2013

(54) METHOD OF MOUNTING OBJECTS TO POLYMERIC MEMBRANES

(76) Inventor: Joel A. Stanley, Colleyville, TX (US)

( * ) Notice: Subject to any disclaimer, the term of this patent is extended or adjusted under 35 U.S.C. 154(b) by 241 days.

(21) Appl. No.: 13/043,052

(22) Filed: Mar. 8, 2011

(65) Prior Publication Data

US 2011/0162779 A1 Jul. 7, 2011

Related U.S. Application Data

(63) Continuation-in-part of application No. PCT/US2010/048734, filed on Sep. 14, 2010, and a continuation-in-part of application No. 12/559,117, filed on Sep. 14, 2009, now Pat. No. 7,935,202.

(51) Int. Cl.
*E04D 5/06* (2006.01)
*E04D 5/14* (2006.01)
*B32B 37/00* (2006.01)

(52) U.S. Cl.
USPC .............................................. 156/71; 156/291

(58) Field of Classification Search
None
See application file for complete search history.

(56) References Cited

U.S. PATENT DOCUMENTS

| | | | |
|---|---|---|---|
| 4,389,826 A | 6/1983 | Kelly | |
| 4,657,802 A * | 4/1987 | Morman | 428/152 |
| 4,747,241 A | 5/1988 | Whitman | |
| 4,778,702 A | 10/1988 | Hutter et al. | |
| 5,316,834 A | 5/1994 | Matsuda et al. | |
| 5,349,791 A | 9/1994 | Zaleski | |
| 5,572,843 A | 11/1996 | Jordan | |
| 5,762,720 A | 6/1998 | Hanoka et al. | |
| 5,921,973 A * | 7/1999 | Newkirk et al. | 604/365 |
| 5,986,203 A | 11/1999 | Hanoka et al. | |
| 6,046,399 A | 4/2000 | Kapner | |
| 6,110,311 A | 8/2000 | Mayle et al. | |
| 6,124,016 A | 9/2000 | Weil | |
| 6,167,717 B1 | 1/2001 | Dudley et al. | |
| 6,177,161 B1 | 1/2001 | Riom et al. | |
| 6,230,461 B1 | 5/2001 | Piront | |
| 6,238,502 B1 | 5/2001 | Hubbard | |
| 6,453,964 B1 | 9/2002 | Pfotenhauer et al. | |
| 6,554,947 B2 | 4/2003 | Pfotenhauer et al. | |
| 6,640,511 B1 | 11/2003 | Link | |
| 6,883,336 B2 | 4/2005 | Dudley et al. | |
| 7,900,413 B2 | 3/2011 | Stanley | |
| 2001/0030380 A1 | 10/2001 | Fujihira | |
| 2005/0183346 A1 | 8/2005 | Dudley et al. | |
| 2007/0175170 A1 | 8/2007 | Shah | |
| 2009/0151869 A1 | 6/2009 | Peterson | |

OTHER PUBLICATIONS

Advertisement for Applied Energy Technologies (Date Unknown).

(Continued)

*Primary Examiner* — Barbara J Musser
(74) *Attorney, Agent, or Firm* — James E. Walton; Richard G. Eldredge

(57) ABSTRACT

A system and method to attach an object to a support structure. The system includes an object attached to an elastic membrane. The elastic membrane includes a lower surface having a first and a second surface area. The first surface area extends peripherally along at least a portion of the lower surface and the second surface area is at least partially enclosed within the first surface area and separable from the support structure. The system further includes an absorbent material attached to the first surface area and an adhesive applied to a top surface of the support structure. The absorbent material being adapted to bond with at least a portion of the adhesive.

3 Claims, 23 Drawing Sheets

(56) References Cited

OTHER PUBLICATIONS

Online Advertisement for EcoFasten Solar (as of Jul. 31, 2009).
Online Advertisement for Architecture Yamade from www.a-yamade.co.jp: (Date Unknown).
Notice of Allowance dated Feb. 7, 2010 from corresponding U.S. Appl. No. 12/559,117.
Request for Continued Examination dated Oct. 21, 2011 from corresponding U.S. Appl. No. 12/559,117.
Advisory Action dated Jan. 20, 2011 from corresponding U.S. Appl. No. 12/559,117.
Amendment After Final dated Jan. 13, 2011 from corresponding U.S. Appl. No. 12/559,117.
Final Office Action dated Dec. 21, 2010 from corresponding U.S. Appl. No. 12/559,117.
Interview Summary dated Dec. 15, 2010 from corresponding U.S. Appl. No. 12/559,117.
Amendment dated Dec. 13, 2010 from corresponding U.S. Appl. No. 12/559,117.
Office Action dated Dec. 9, 2010 from corresponding U.S. Appl. No. 12/559,117.
The International Search Report and the Written Opinion of the International Searching Authority from counterpart International Application No. PCT/US2010/048734, filed Sep. 14, 2010, issued by the International Searching Authority on Nov. 3, 2010.
Advertisement for Eco-Fasten, "Bulls Eye Target Patch" (as of Mar. 2011).
International Preliminary Report on Patentability International Application No. PCT/US10/48734, issued by the International Preliminary Examining Authority on Dec. 5, 2011.

* cited by examiner

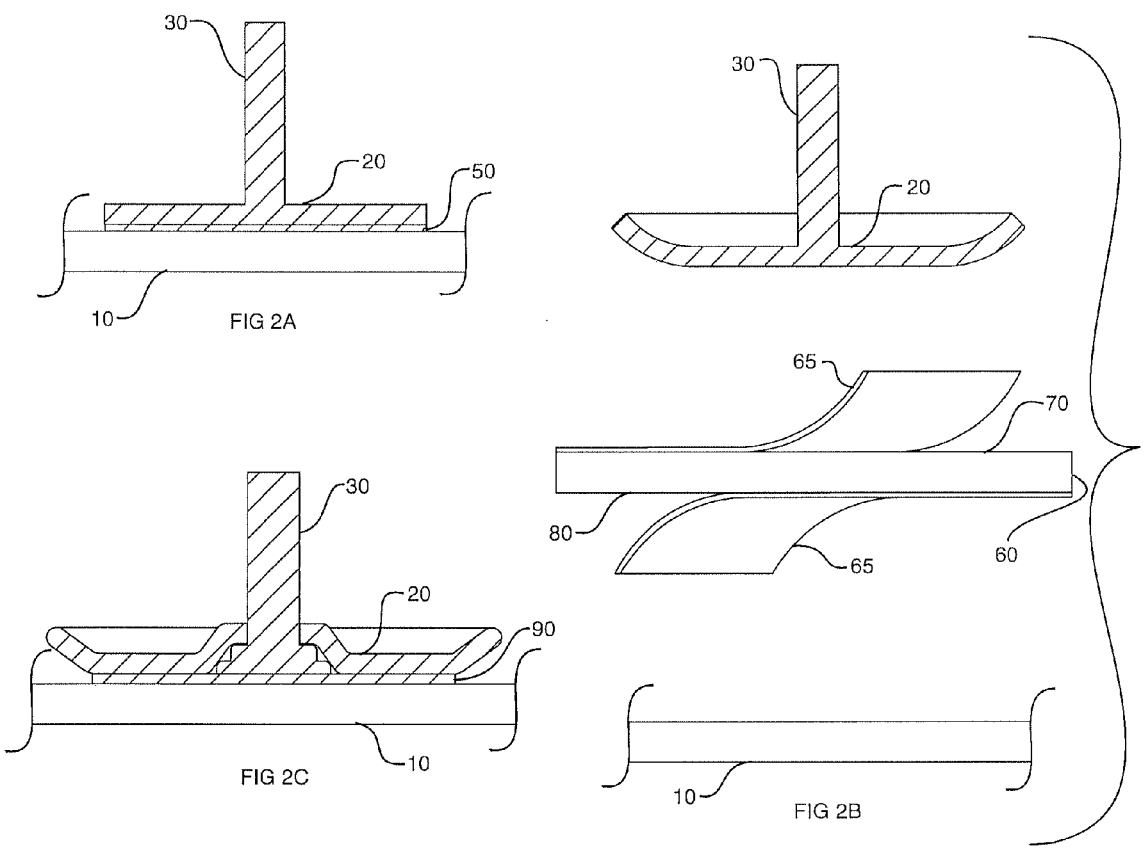
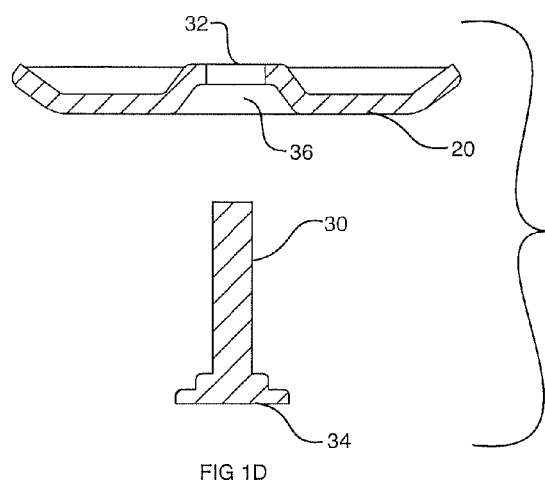

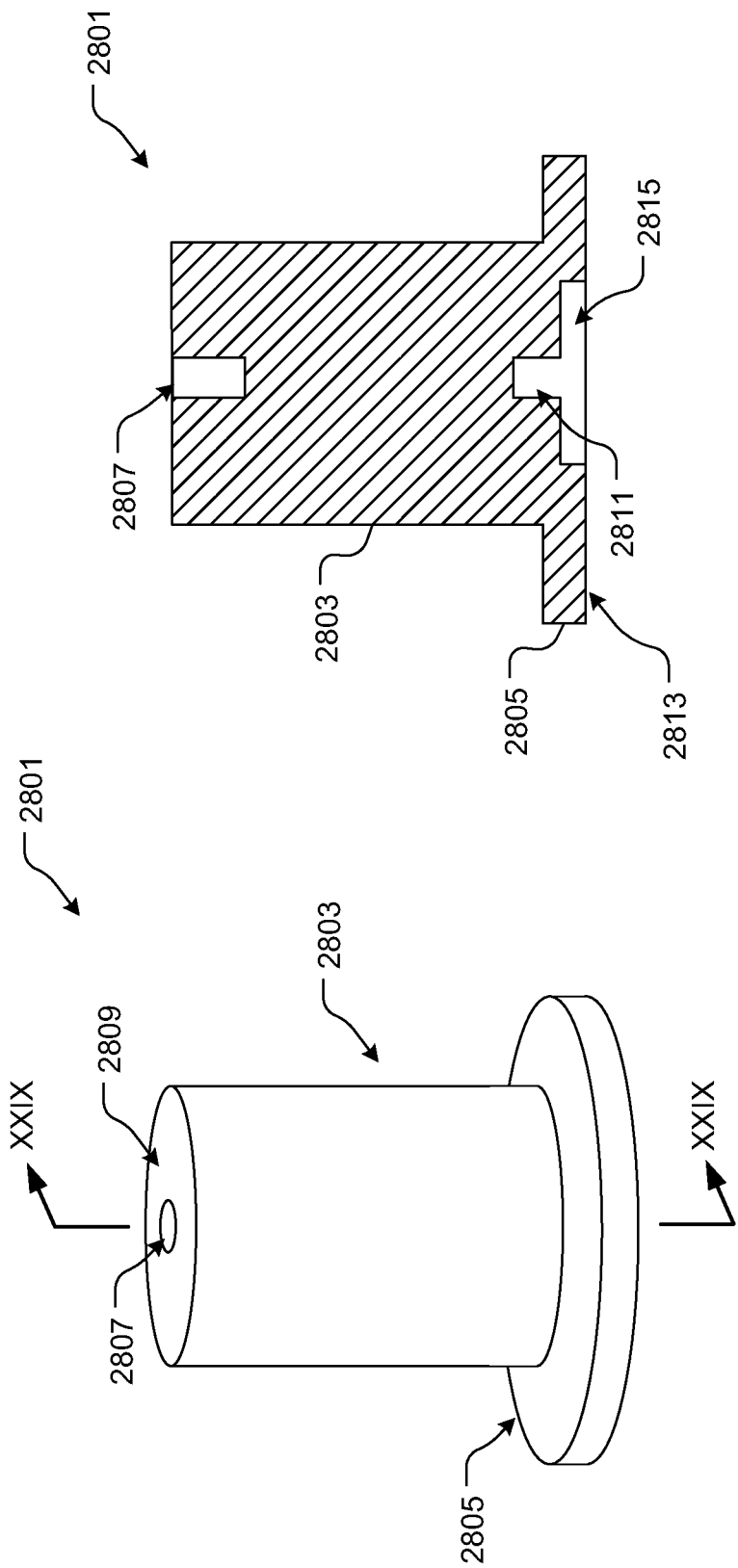

METHOD OF MOUNTING OBJECTS TO POLYMERIC MEMBRANES

CROSS REFERENCE TO RELATED APPLICATIONS

This application is a continuation-in-part of U.S. application Ser. No. 12/559,117, filed 14 Sep. 2009, now U.S. Pat. No. 7,935,202, titled "System for Mounting Objects to Polymeric Membranes," and is a continuation-in-part of International Application No. PCT/US10/48734, filed 14 Sep. 2010, titled "System for Mounting Objects to Polymeric Membranes," which claims the benefit of U.S. application Ser. No. 12/559,117, filed 14 Sep. 2009, titled "System for Mounting Objects to Polymeric Membranes;" both of which are both hereby incorporated by reference for all purposes as if fully set forth herein.

BACKGROUND

1. Field of the Present Description

The present description relates to methods and system for mounting objects to polymeric membranes.

2. Description of Related Art

Various applications exist in which a polymeric membrane may be placed over a surface. For example, it may be desirable to provide a polymeric membrane as a roofing material. That is, a polymeric membrane may be applied to an outer surface of a building structure, such as a roof, to protect the structure from the environment.

DESCRIPTION OF THE DRAWINGS

The novel features believed characteristic of the invention are set forth in the appended claims. However, the invention itself, as well as a preferred mode of use, and further objectives and advantages thereof, will best be understood by reference to the following detailed description when read in conjunction with the accompanying drawings, wherein:

FIG. 1D shows a cross-sectional view of an example mounting plate;

FIG. 2A is a cross-sectional view of an example mounting system including a mounting plate secured to polymeric membrane with an adhesive;

FIG. 2B shows an exploded view in cross section of an example mounting system with a tape including adhesive on opposing sides thereof;

FIG. 2C shows a cross-sectional view of a further example mounting system.

FIG. 28 is an oblique view of a riser according to an alternative embodiment of the present invention;

FIG. 29 is a cross-sectional front view of the riser of FIG. 28 taken at XXIX-XXIX;

Figure 1A:
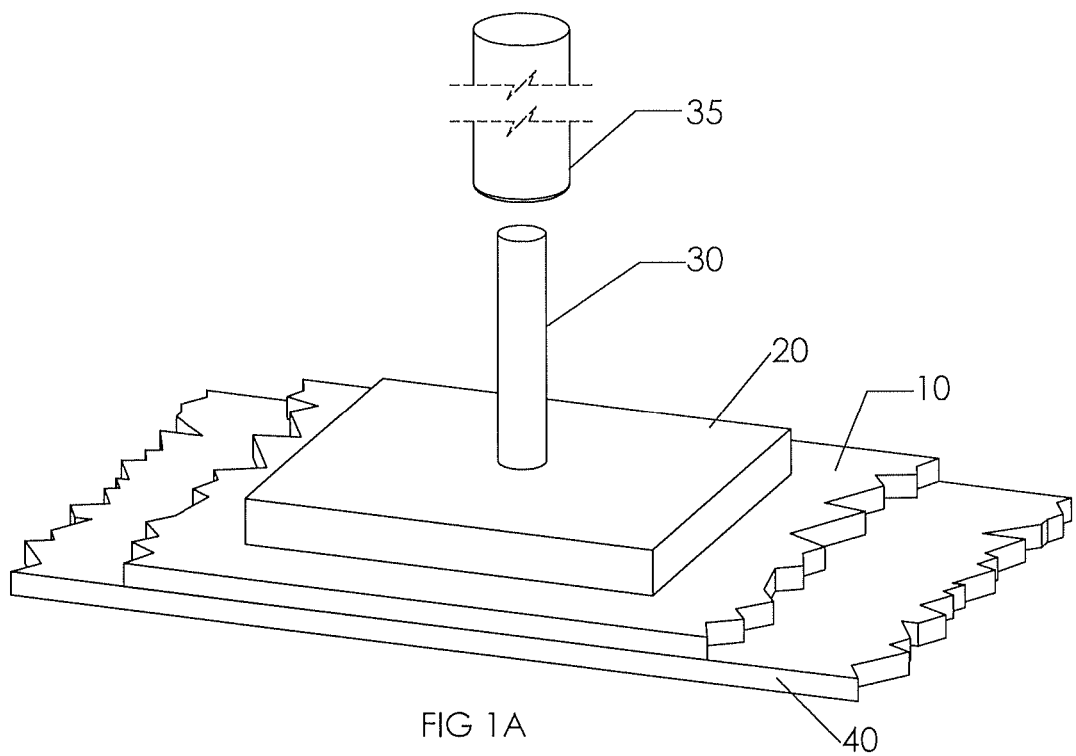
FIGS. 1A-1C show an example systems for attaching a mounting plate to a polymeric membrane.

While the mounting system of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the process of the present application as defined by the appended claims.

DETAILED DESCRIPTION

The present disclosure describes methods and systems for mounting or otherwise attaching an object to polymeric membranes. For example, in some instances, the present disclosure describes methods and systems for attaching objects to polymeric membranes utilized for covering all or a portion of a building structure roof. In some instances, the polymeric membranes may include thermoplastic polymeric membranes ("thermoplastic membranes"), while, in other instances, the polymeric membranes may include thermoset polymeric membranes ("thermoset membranes"). Example objects that may be attached include photovoltaic cells, an air handling component (e.g., air conditioning or heating components), telecommunications equipment (e.g., antennas, satellite dishes, etc.), or any other desired object. It should be understood that the materials described herein provide sufficient elasticity for the features described below.

Utilizing the described systems and methods for securing one or more photovoltaic cells to the roof of a structure may provide tax benefits. For example, tax benefits may exist for having photovoltaic cells attached to the structure of a roof that are otherwise unavailable for photovoltaic cells that are merely placed on a roof unattached to the roof structure. Thus, in some implementations, the system and methods described herein provide for attaching an object to the roof structure, and, in the case of photovoltaic cells, may enable a user to enjoy the available tax benefits associated therewith.

In other implementations, the described methods and systems may be utilized for attaching objects to a polymeric membrane forming part of a structure. Further, while some implementations may be described with respect to thermoplastic membranes, thermoset membranes may also be applicable and vice versa. In general, the described methods and systems may be applicable to applications including roofing, waterproofing, earth lining, pond lining, tent construction, tension fabric applications, air forming technologies, flexible plastic forming (such as with flexible plastic films), rigid plastic forms, as well as any other suitable application.

FIG. 1A shows a perspective view of an example implementation of a system for mounting an object to a polymeric membrane. FIG. 1A shows a polymeric membrane (interchangeably referred to as "membrane") 10 and a mounting plate 20. In some instances, the polymeric membrane 10 is a thermoplastic membrane. Example thermoplastic membranes may include polyvinyl chloride (PVC), thermoplastic olefins (TPO), keytone ethylene esters (KEE), nitrile butadiene polymers (NBP), as well as other suitable thermoplastics. In other instances, thermoset membranes may also be used. For example, examples thermoset membranes may include membranes formed from ethylene propylene diene monomer (EPDM) as well as any other suitable thermoset membranes, including thermoplastic membranes that may morph into thermoset membranes over time, such as chlorosulfonated polyethylene (CSPE).

The polymeric membrane 10 may be secured to a structure 40, such as a roof structure. The polymeric membrane 10 may be secured to the structure 40 in any known or suitable manner. Further, in some instances, the mounting plate 20 may be formed entirely or in part from a metal, such as steel, galvanized steel, aluminum, titanium, or other desired or suitable metal. Additionally, the mounting plate 20 may or may not be weatherized. In other instances, the mounting plate 20 may be formed from other materials, such as glass, plastic, ceramics, composite materials, or any other material. It should be appreciated that some applications may not require polymeric membrane 10; as such, mounting plate 20 may be bonded or attached directly to structure 40 without the use of polymeric membrane 10.

As shown, the mounting plate 20 has a protrusion 30 extending therefrom that may be used for securing a structure. The protrusion 30 may allow attachment and detachment of the structure, such as structure 35, without damage or alteration to the polymeric membrane 10. For example, in some instances, the protrusion 30 may provide for a threaded connection with structure 35, although any other suitable connection mechanism may be used. In other implementations, the mounting plate 20 may be integral to a structure. In still other implementations, the mounting plate 20 may omit the protrusion 30. Alternately, the mounting plate 20 may include a mechanism for attaching or detaching a corresponding structure thereto. For example, the mounting plate 20 may include an interlocking mechanism for accepting one or more structures. Example structures may include one or more photovoltaic cells, air handling equipment (e.g., air conditioning equipment or heating equipment), one or more antennas, mounting structures therefor, a barrier, or any other desired structure.

Figure 1B:
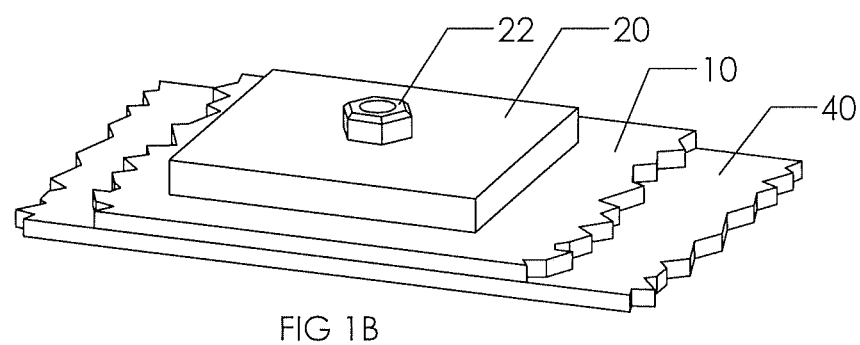
Figure 1C:
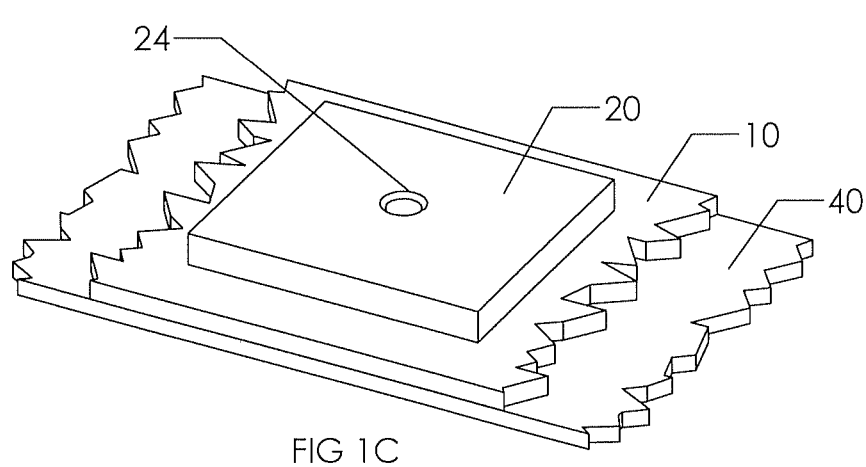

In still other implementations, an example mounting plate 20 may include a threaded portion for mating engaging with a corresponding threaded portion provided on a structure to be attached or otherwise coupled to the mounting plate 20. For example, FIG. 1B shows a mounting plate 20 that includes a welded nut 22 for accepting a protrusion having mating threads. Alternately, as shown in FIG. 1C, the mounting plate 20 may have a threaded portion 24 formed therein for accepting the protrusion.

FIG. 1D shows a cross-sectional view of another example mounting plate 20 in which the protrusion 30 is a separate piece insertable into an opening 32 formed in the mounting plate 20. Further, a head 34 of the protrusion 30 may be retained in a pocket 36 formed in the mounting plate 20. In other instances, the head 34 may not be retained in a pocket formed in the mounting plate 20. In some implementations, the protrusion 30 may be a carriage bolt insertable into the opening 32, and the interface between the opening 32 and the protrusion 30 prevents the protrusion 30 from rotating relative to the mounting plate 20. Further, a mounting plate 20 having an opening 32 of a single size may be operable to accept protrusions 30 having varying shaft lengths, widths, and/or diameters.

The mounting plate 20 may be attached to the polymeric membrane 10 in numerous ways. FIGS. 2A-2C show several cross sectional views of the mounting plate 20 attached to the polymeric membrane 10. For example, FIG. 2A shows the mounting plate 20 attached to the membrane 10 with a binding agent, such as an adhesive 50, disposed therebetween. Alternately, the binding agent for securing the mounting plate 20 may be a carrier tape 60 having adhesive 70, 80 provided on opposing sides thereof, as shown in FIG. 2B. In some implementations, the carrier tape 60 may have a removable protective film or backing 65. In some instances the adhesive 70 and adhesive 80 may be the same adhesive, while, in other instances, the adhesives 70, 80 may be different. For example, adhesives 70, 80 may be selected based on the material being adhered. For example, for a mounting plate 20 formed from steel, the adhesive 70 may be selected to adhere steel, while, for a membrane 10 formed from PVC, the adhesive 80 may be selected to adhere to PVC. In some instances the carrier tape 60 may be a foam-based tape. Carrier tape 60 may be used to secure the mounting plate 20 to the membrane 10. One or more tape strips or sheets may be used to secure the mounting plate 20. Further, the carrier tape 60 may be custom shaped and/or formed to fit to geometry of the mounting plate 20. For example, the carrier tape 60 may be custom fit to correspond to one or more geometric features of the mounting plate 20, such as protrusions or other topographical shapes.

Multiple options for adhesives 50, 70, and 80 are available and selecting an appropriate adhesive is often dependent upon the desired engineered failure during testing. In some instances, it may be desirable for the adhesion provided by the selected adhesive to give way at a chosen weight threshold preventing damage to other components within the assembly. In other instances, it may be desirable for the adhesive bond to be so strong that components would not separate without damage to one surface or another. In addition, the selected adhesive may be applied to a carrier tape, the carrier tape and selected adhesive also being capable of being engineered with a chosen weight threshold and thickness. Adhesives 50, 60, and 70 include cross linking as well as non-cross linked butyl adhesives. A non-exclusive list of adhesives 50, 70, and 80, as well as carrier tapes 60, that may be used are: 3M VHB 4941 F, 3M VHB 4941, 3M VHB 4932, 3M VHB 4952, 3M VHB 5925, 3M VHB 5952, 3M VHB 5962, 3M weather strip tapes, 3M Polyurethane 560, 3M Hybrid Sealant 760, 3M DP 190, 3M DP 125, and 3M 1099 Scotch Weld Adhesive, all of which are produced by 3M of 3M Center, St. Paul, Minn. 55144. Additionally, Ashland Aroset 1930 produced by Ashland Inc of Covington, Ky. 41012 is another example of a suitable adhesive. Further, SikaLastomer-68 produced by Sika Corporation of Madison Heights, Mich. 48071, is example of a suitable carrier tape. The following companies make similar or competing adhesive to those named above: Carlisle Syntec of Carlisle, Pa., Carlisle Hardcast Incorporated of Wylie, Tex., and Firestone Building Products of Indianapolis, Ind. It should be appreciated that the adhesives and carrier tapes identified above may be identified as adhesives alone, or as carrier tape alone, or any combination of carrier tape and adhesive.

FIG. 2C shows another example implementation in which the binding agent may be a coating of thermoplastic material 90 applied to one or more surfaces of the mounting plate 20 placed into contact with the polymeric membrane 10. For example, the polymeric membrane 10 may be a thermoplastic membrane. The mounting plate 20 may be located at a desired location on the polymeric membrane 10, and the coating 90 may be heated to form a bond between the mounting plate 20 and the polymeric membrane 10. In some instances, the coating 90 may be heated by heating the mounting plate 20, such as with a thermoinduction welder or hot iron. In other instances, energy may be applied more directly to the coating 90, such as with sonic welding. For example, the mounting plate 20 may be affixed using the coating 90 such as by dielectrical or sonic or vibration welding, solvent bonding, heat bonding (such as using induction heating, infra red heating, hot air heating, or hot iron heating), any combination of the above, or in any other suitable manner.

It should be appreciated that thermoplastic coating 90, as well as the thermoplastic coatings described in the other embodiments herein, may be represented in a variety of forms. Such forms include, but are not limited to: solids, liquids, or any mixtures of material phases suitable for the implementations disclosed herein.

Figure 3:
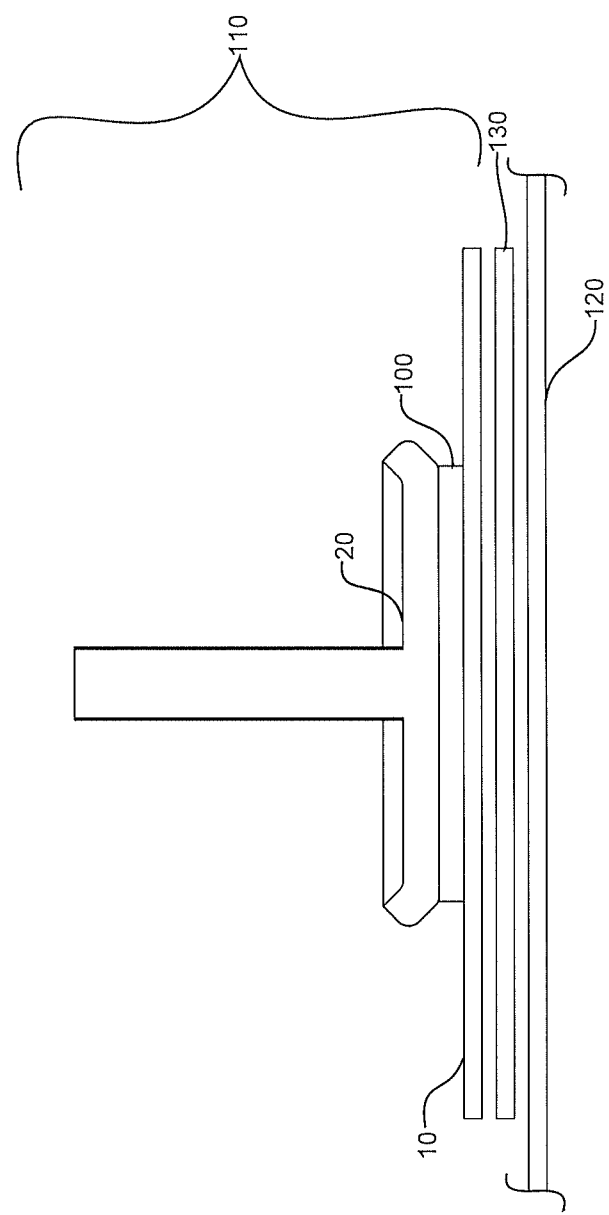
FIG. 3 shows an example mounting assembly that may be coupled to a polymeric membrane.

A further example mounting system is shown in FIG. 3. FIG. 3 shows a mounting plate 20 secured to a polymeric membrane 10 (e.g., a thermoplastic membrane) with a binding agent 100. According to various implementations, the binding agent 100 may be, for example, a coating of thermoplastic material applied to a contact surface of the mounting plate 20. With the thermoplastic coating, the mounting plate 20 may be located at a desired location on the polymeric membrane 10 and heated to bind the mounting plate 20 to the polymeric membrane 10. Alternatively, any adhesive or carrier tape, such as the adhesives and carrier tapes described above, may be used to secure the mounting plate 20 to the membrane 10. The combination of the mounting plate 20 and the polymeric membrane 10 may be considered a mounting assembly 110.

Referring still to FIG. 3, the mounting assembly 110 may be attached to a polymeric membrane 120. In the present example, the polymeric membrane 120 may be a thermoplastic membrane. However, in other instances, the polymeric membrane 120 may be a thermoset membrane. The mounting assembly 110 may be attached to the polymeric membrane 120 in numerous ways. For example, the polymeric membrane 10 of the mounting assembly 110 may be coupled to the polymeric membrane 120 using one or more of the methods described above in regards to the bonding of mounting plate 20 to polymeric membrane 10. In other instances, a bonding agent 130, such as a carrier tape and/or adhesive (such as the carrier tape and adhesive, described respectively above) may be used. It should be appreciated that bonding agent 130 may be another bonding medium, including various bonding materials or various bonding members. Similar to above, the carrier tape may be applied in pieces, such as one or more strips or sheets. Further, as also described above, the carrier tape may be formed to correspond to geometry of the mounting assembly 110.

Figure 4:
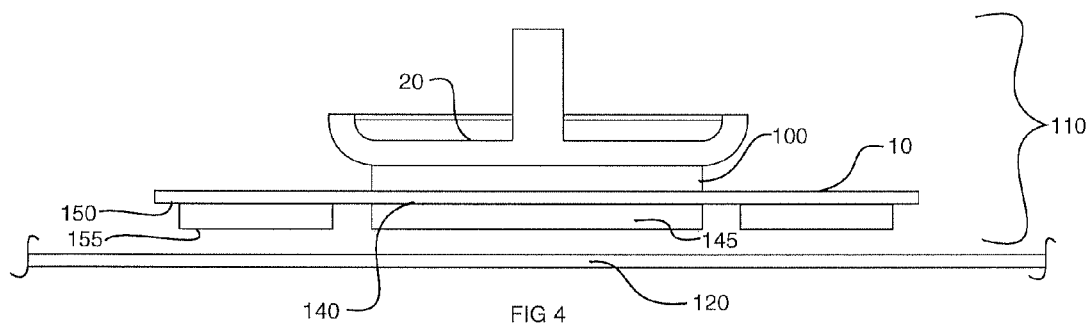
FIG. 4 shows another example mounting assembly that may be coupled to a polymeric membrane.
Figure 5:
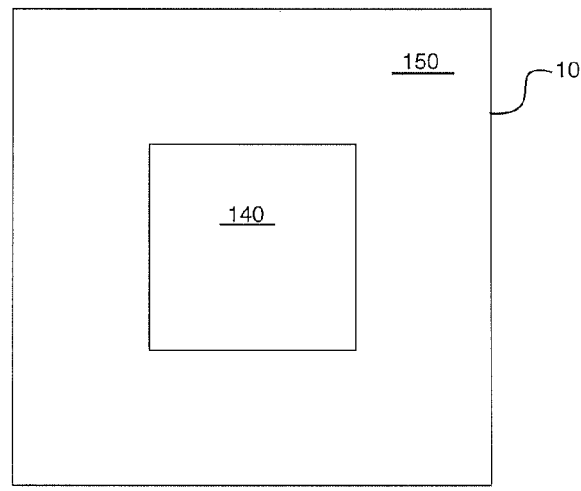
FIG. 5 is a bottom view of the mounting assembly shown in FIG. 4.

FIGS. 4 and 5 illustrate an alternate implementation for securing the mounting assembly 110 to the polymeric membrane 120. As shown, a central portion 140 of the mounting assembly 110 may be secured to the polymeric membrane 120 with an adhesive material 145, such as one or more pieces of carrier tape or adhesive, such as the carrier tape and adhesive described above. Another attachment method or material may be used around a perimeter portion 150. For example, a coating of thermoplastic material 155 at one or more locations along the perimeter portion 150 may be used to secure the perimeter portion 150 to the polymeric membrane 120. The coating of thermoplastic material 155 may be bonded using one or more of the methods described above. Alternately, one or more of an adhesive or carrier tape may be used on the perimeter portion 150. For example, the bonding material used on the perimeter portion 150 may act to further secure the mounting assembly 110 or as a waterproofing material.

It is noted that, in some instances, a coating of thermoplastic material may be used to bond one thermoplastic membrane to another same or similar thermoplastic membrane. In other instances, the thermoplastic material may be omitted. For example, some thermoplastic membranes may be joined using one or more of the welding techniques above without the aid of a bonding material. On the other hand, a coating of thermoplastic membrane may not be capable of bonding a thermoplastic membrane or thermoset membrane to another thermoset membrane. In such instances, an adhesive, such as an adhesive or carrier tape may be used to bond such dissimilar materials to each other.

In some instances, the polymeric membrane 120 may be the same or a similar thermoplastic as a thermoplastic forming the thermoplastic membrane 10, such as one or more of the thermoplastics described above. However, the thermoplastics forming the respective thermoplastic membrane 10 and the thermoplastic membrane 120 may be different while still bondable with or without the use of a thermoplastic material. In some instances, the thermoplastic membrane 120 may form an outer surface of a roof structure. However, the description is not so limited, and the present description may be applicable to a thermoplastic membrane in any desired application.

Figure 6:
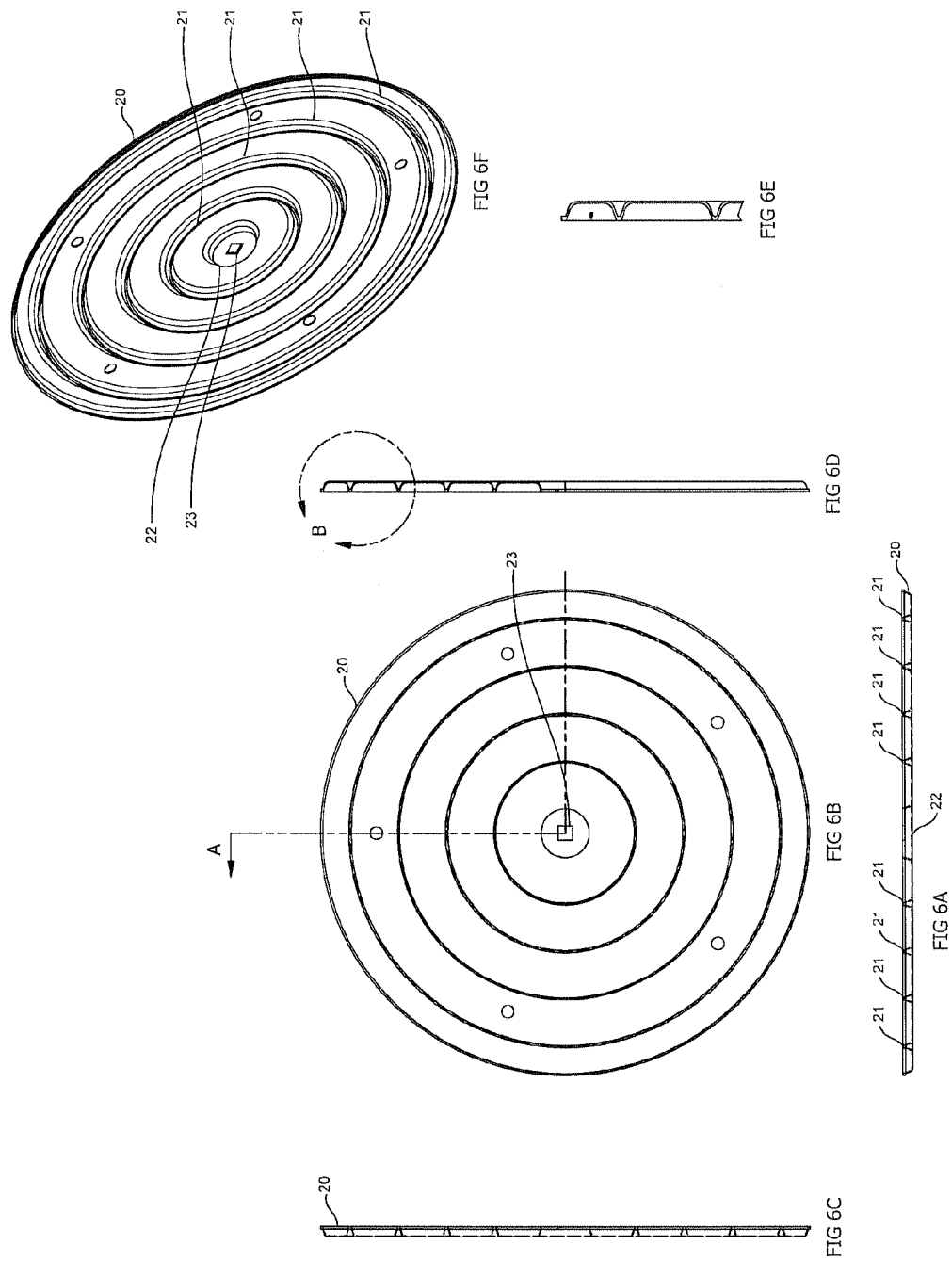
FIGS. 6A-F, 7A-E, and 8A-D show various views of example mounting plates.
Figure 7:
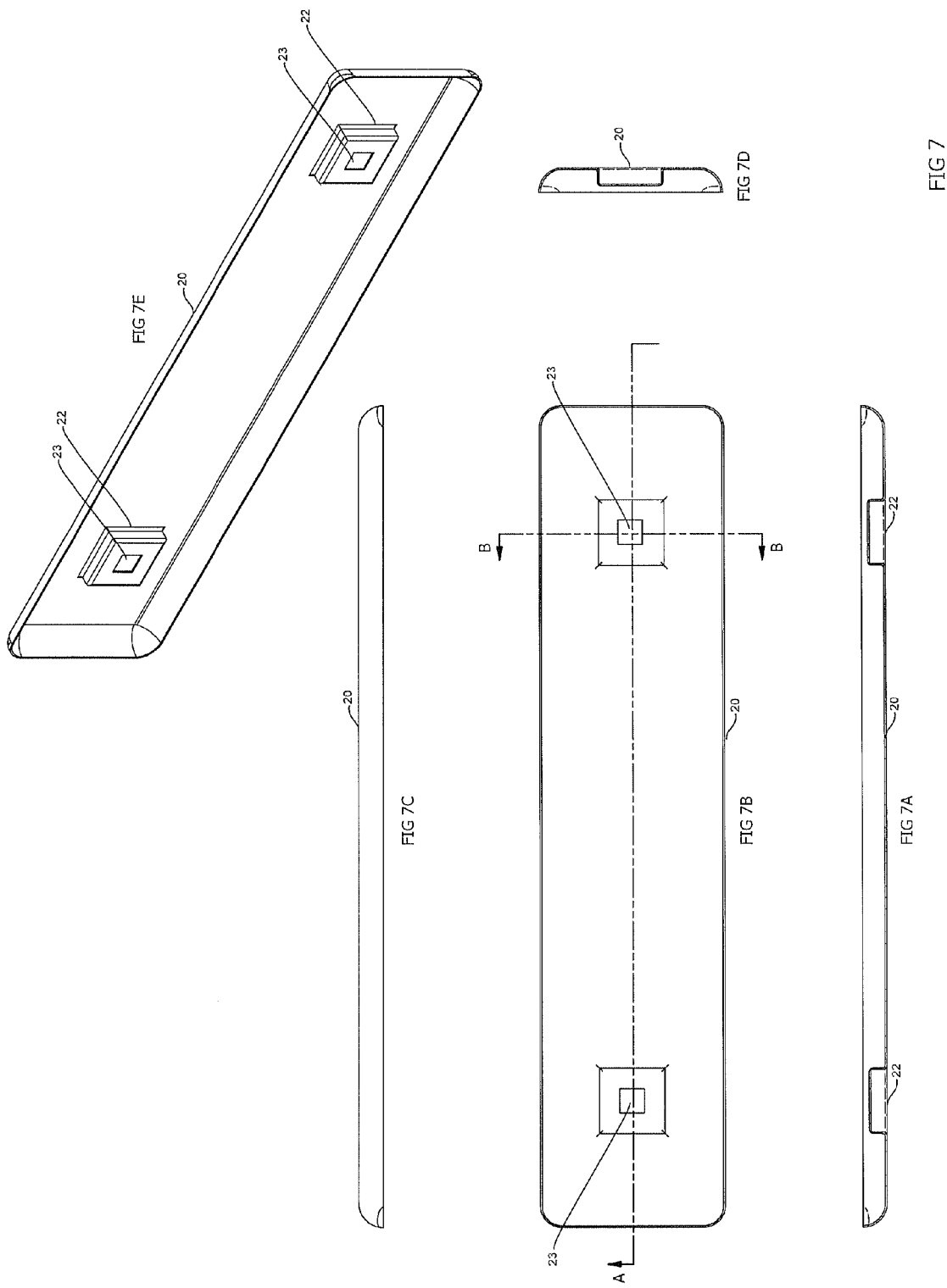
Figure 8:
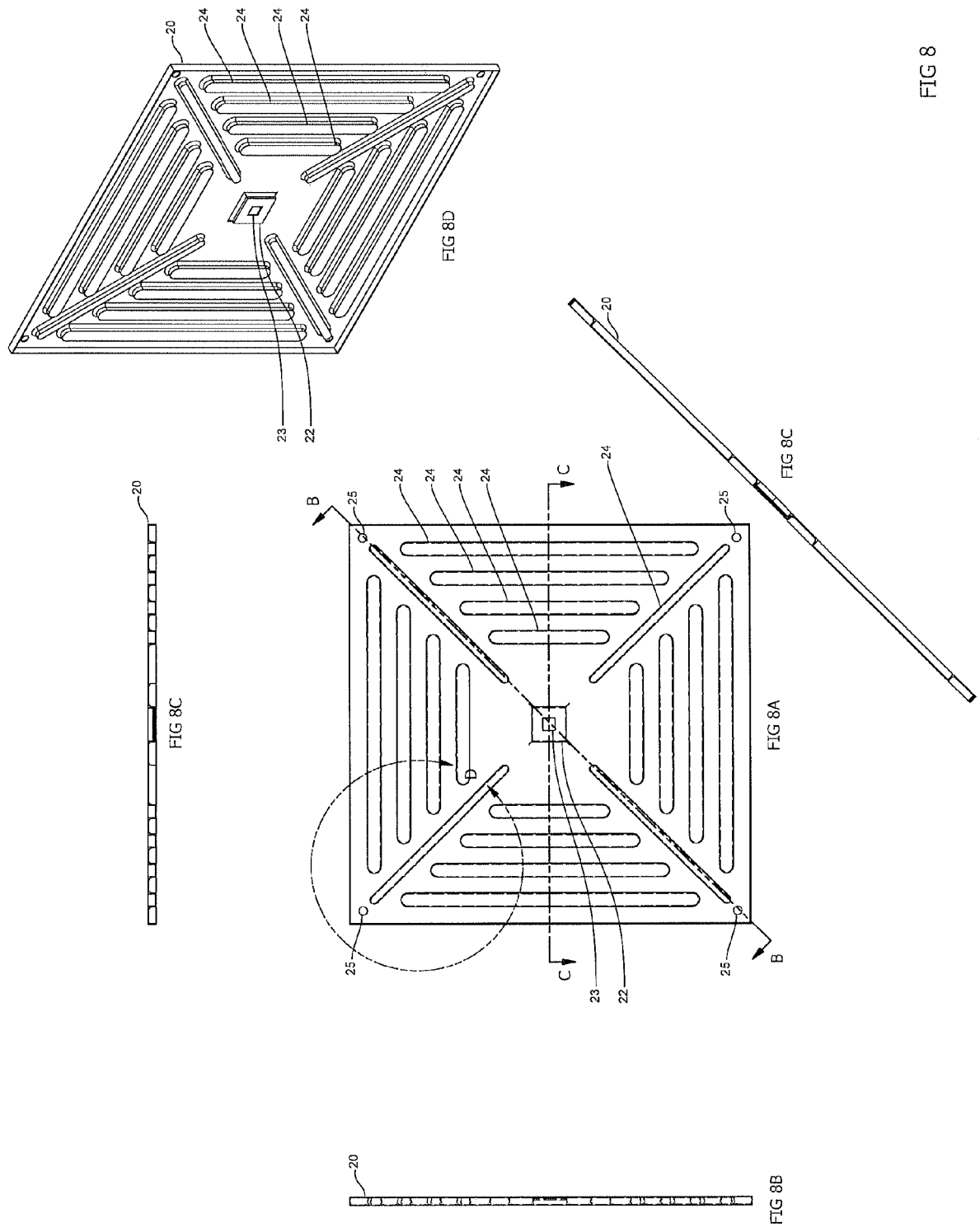

The mounting plate 20 may be of any desired shape. For example, the mounting plate may be circular, rectangular, square, elongated, or be of any other size or shape. Example mounting plates are illustrated in FIGS. 6-8. FIGS. 6A-6E show various views of a circular mounting plate 20 having a plurality of concentric ridges 21 formed therein as well as a central cavity 22 that may be used to capture a head of a protrusion, as discussed in a similar manner above. As also described above, the central cavity 22 may accept a protrusion of different sizes. The protrusion may extend through opening 23.

Referring to FIGS. 7A-E, the example mounting plate 20 also includes cavities 22 to accept the heads of protrusions. The protrusions may extend through openings 23 formed in a wall of the cavities 22. FIGS. 8A-D are various views of another example mounting plate 20. The mounting plate 20 may include various ridges 24 formed therein along with a cavity 22 and opening 23. Again, the cavity 22 may be used to capture an end portion of a protrusion extending through the opening 23. The mounting plate 20 may also include openings 25 formed around a periphery thereof.

Further, for the example mounting plate 20 shown in FIGS. 6A-8D along with others within the scope of the disclosure, the cavities 22, openings 23, and/or the combination thereof may be operable to prevent rotation of the protrusion relative to the mounting plate 20 while also accepting protrusions of different sizes. Additionally, the respective sizes of the ridges 24, openings 23, cavities 22, as well as other aspects of the mounting plates 20 may be altered to any desired size.

Figure 9:
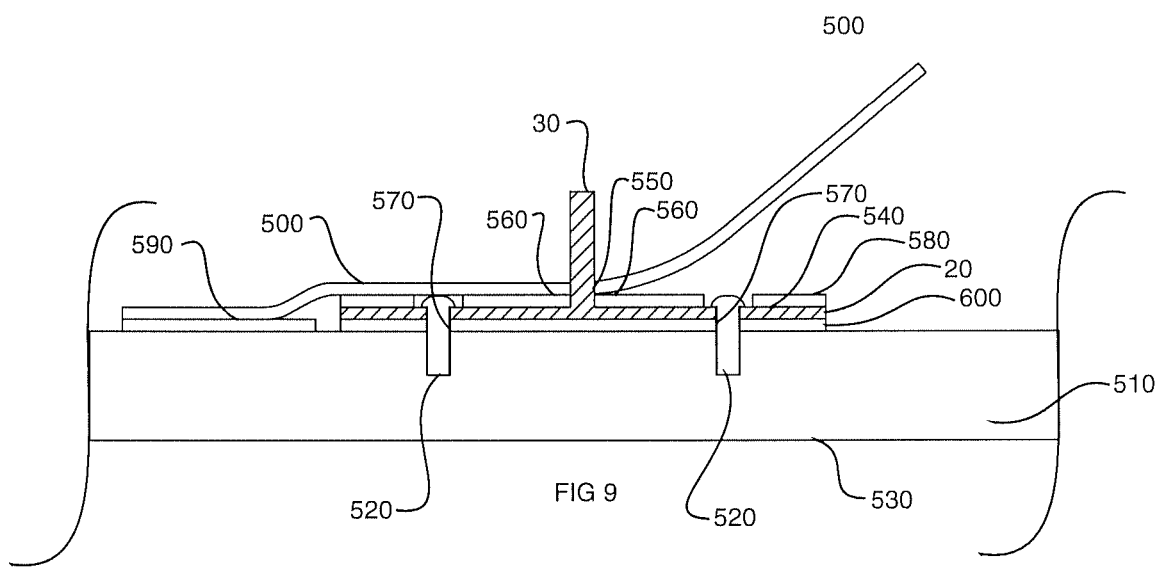
FIG. 9 shows a cross-sectional view of a further example mounting system.

Another example mounting system is shown in FIG. 9 in which a mounting plate 20 is disposed between a first polymeric membrane 500 and a second polymeric membrane 510. Fasteners 520 extend through the mounting plate 20, the second polymeric membrane 510, and into a substructure 530. The first polymeric membrane 510 overlays a first surface 540 of the mounting plate 20 and includes an opening 550 through which the protrusion 30 extends. A bonding material 560 may be used to adhere the first polymeric membrane 500 to the mounting plate 20.

In some instances, the bonding material 560 may be a coating of a thermoplastic material applied to a portion of the first surface 540 between the protrusion 30 and openings 570 formed in the mounting plate 20 through with the fasteners 520 extend. Still further, in some instances, the bonding material 560 may be applied and the first polymeric membrane 500 coupled therewith to the mounting plate 20 during one or more manufacturing processes. That is, bonding the first polymeric membrane 500 to the mounting plate 20 with the bonding material 560 may be performed remote from a job site, such as at a manufacturing facility. In other instances, the first polymeric membrane 500 may be bonded to the mounting plate 20 with the bonding material 560 at a jobsite. The bonding material 560 may be a coating of thermoplastic material and used to bond the two components in one or more of the methods described above. In addition to adhering the first polymeric membrane 500 to the mounting plate 20, the bonding material 560 may also form a seal preventing or substantially preventing fluids from penetrating through the opening 550 formed through the openings 570 and into the substructure 530.

A bonding material 580 may also be applied to the first surface 540 of the mounting plate 20. In some instances, the bonding material 580 may also be used to secure the first polymeric membrane 500 to the mounting plate 20, such as after the fasteners 520 have been used to secure the mounting plate 20 to the substructure 530. Utilizing the bonding material 580 after fasteners 520 have been applied avoids the need to puncture the first polymeric membrane 500 for the fastener 570. Thus, in some instances, the bonding material 560 may be used to secure only a portion of the first polymeric membrane 500 to the mounting plate 20 while still allowing passage of the fasteners 520 through the openings 570 without the need to puncture the first polymeric membrane, 500. The bonding material 580 may be utilized thereafter to secure the first polymeric membrane 500 to the mounting plate 20 thereby also providing a seal. The first polymeric membrane 500 may also be secured to the second polymeric membrane 510 with a bonding material 590. Also, a coating or bonding material may be omitted where the polymeric membranes are capable of being joined without such materials. For example, the membranes may be thermoplastic membranes capable of being joined using one or more of the bonding techniques described above. In such instances, the bonding material 590 may be omitted.

Figure 10:
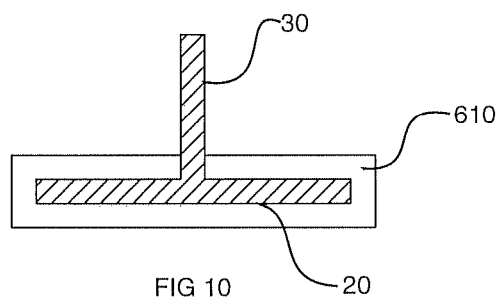
FIG. 10 shows a cross-sectional view of an example mounting plate illustrated in FIG. 9.

A bonding material 600 may also be used to secure the mounting plate 20 to the second polymeric membrane 510. The bonding materials 560, 580, 590, and 600 cooperate to form a seal around the mounting plate 20 to aid in preventing or substantially reducing penetration of fluids and/or debris into the substructure 530. One or more of the bonding materials 560, 580, 590, and 600 may be a coating of a thermoplastic material and used to form a bond using one or more of the techniques described above. In some instances, the bonding materials 560, 580, and 590 may be the same material, such as a coating of thermoplastic material 610, and may be applied to the mounting plate 20, as shown in the example of FIG. 10. Alternately, one or more of the bonding materials 560, 580, 590, and 600 may be a carrier tape or adhesive as also described above. In still other implementations, one or more of the bonding materials 560, 580, 590, and/or 600 may be omitted. For example, in some implementations, the polymeric membranes 500, 510 may be secured directly to each other using one or more of the joining techniques described above without the use of a bonding material. Still further, the mounting plate 20 may also be formed from a material that is joinable to one or more of the polymeric membrane 500 and/or polymeric membrane 510 without the use of a bonding agent using one or more of the techniques described above. In such instances, one or more of the bonding materials 560, 580, and/or 600 may be omitted.

The mounting plate 20 is shown with a protrusion 30 includes, although the protrusion 30 may be omitted. Alternately, the mounting plate 20 may be fixedly attached to another object. Still further, the mounting plate 20 may have a mechanism for selectively attaching and detaching another object.

Figure 11:
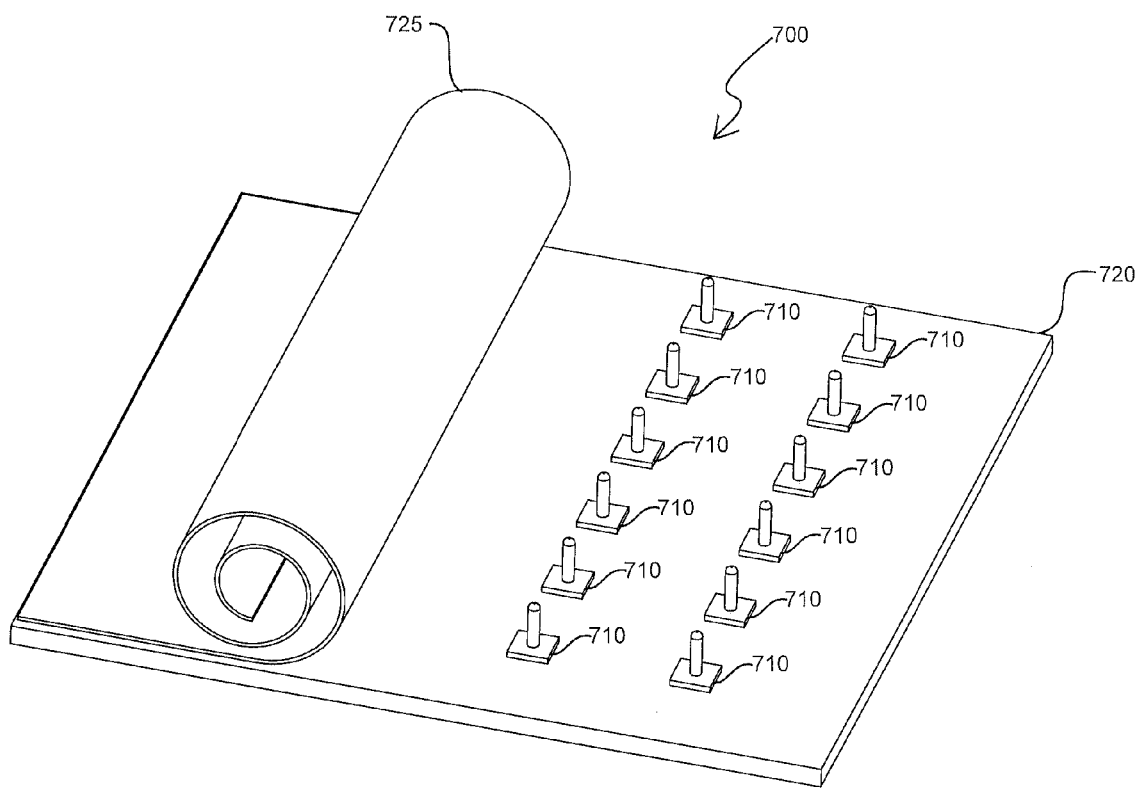
FIG. 11 shows another example mounting system.
Figure 12:
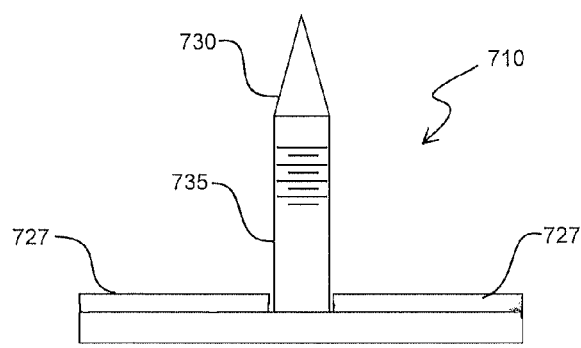
FIG. 12 is a side view of an example mounting plate shown in FIG. 11.

FIGS. 11 and 12 show another example system 700 in which one or more mounting plates 710 are secured to a structure 720. For example, the structure 720 may be a roof structure, although structure 720 is not so limited but may encompass other structures, such as one or more of the structures identified above or other suitable structure. In some instances, the mounting plates 710 may be coupled to the structure 720 with fasteners, although the mounting plates 710 may be attached in other ways. A polymeric membrane 725 is applied over the mounting plates 710, such as by unrolling a roll of the polymeric membrane 725. An example mounting plate 710 is shown in FIG. 12. The mounting plate 710 may include a protrusion 730. Further, in some implementations, the protrusion 730 may include a piercing portion 740 adapted to puncture the polymeric membrane 725. Also, a portion of the protrusion 730 may include a fastening portion 735 that may be used to attach a structure to the mounting plate. For example, in some instances, the fastening portion 735 may be a threaded portion. However other fastening mechanisms may also be used.

One or more of the mounting plates 710 may be secured to the structure 720, such as in an array or any other configuration. The mounting plates 710 may be secured with fasteners and/or with one or more of the techniques described herein (e.g., using a coating of thermoplastic material, carrier tape, adhesive, etc.). With the mounting plates 710 secured to the structure 720, the polymeric membrane 725 may be overlaid. The mounting plate 725 may be made to extend through the polymeric membrane 725 such as by puncturing the polymeric membrane 725 with the piercing portion 740. In other implementations, the polymeric membrane 725 may have preformed openings to allow the protrusions 730 to extend therethrough. The polymeric membrane 725 may be secured to the mounting plate 710 using one or more of the techniques described above. For example, the mounting plate 710 may be coupled to the polymeric membrane 725 with a bonding material 727. The bonding material 727 may be one or more of the materials discussed above and the coupling may be formed using one or more of the methods described above.

Figure 13:
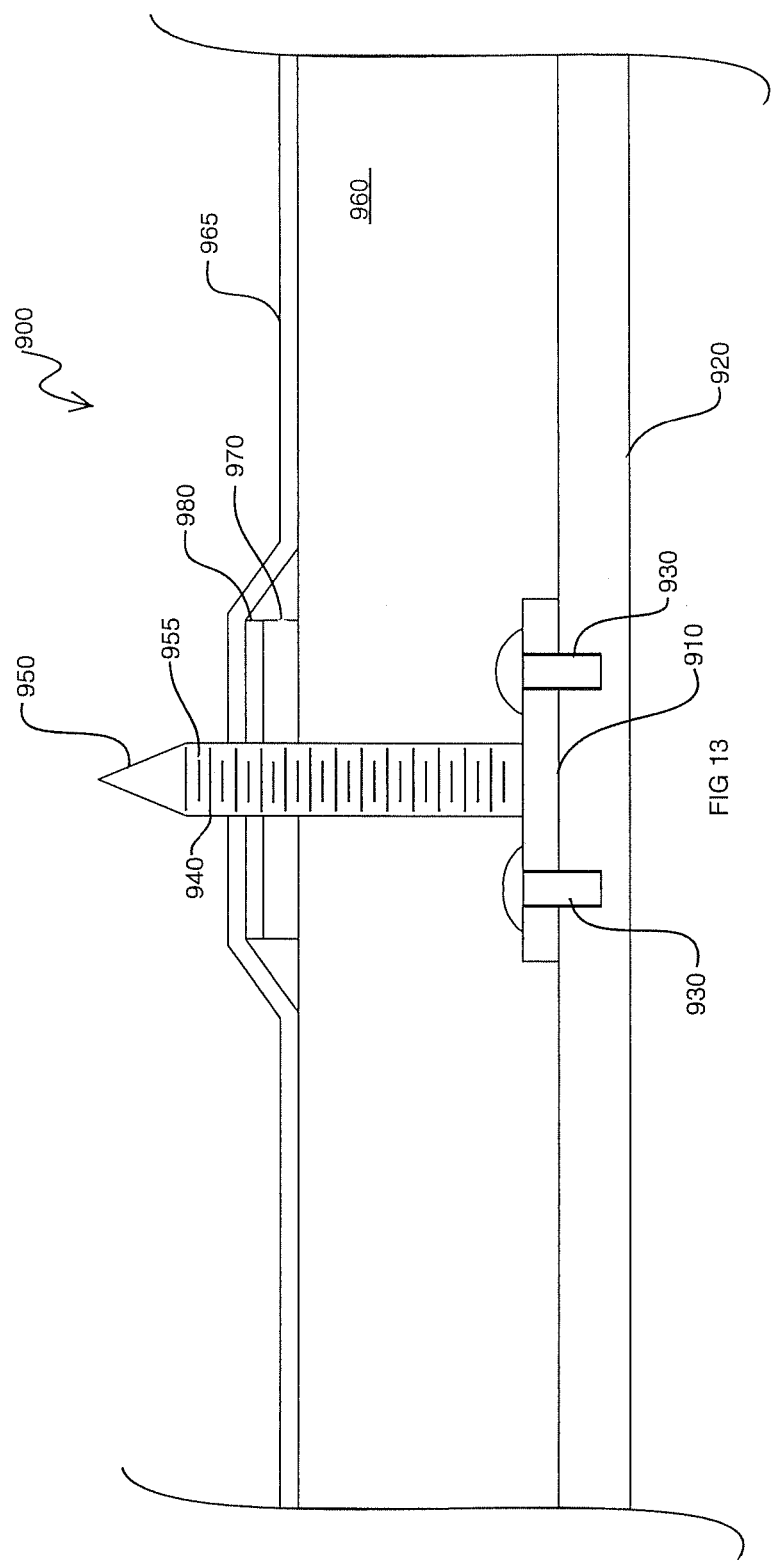
FIG. 13 is a further example mounting system that includes, among other features, an insulating member.

FIG. 13 shows another example system 900 including a mounting plate 910 coupled to a substructure 920. Among other uses, the system 900 may be applicable to roofing applications. The mounting plate 910 is shown as being attached with fasteners 930. However, other techniques may be used to secure the mounting plate 910 to the substructure 920. The mounting plate 910 may include a protrusion 940 and a piercing portion 950. Further, in some implementations, the protrusion 940 may include a fastening portion 955. Additionally, while the protrusion 940 is shown as an integral portion of the mounting plate 910, the protrusion 940 may be attached to the mounting plate 910 using a fastening mechanism. For example, in some implementations, the protrusion 940 may be attached to the mounting plate 910 via a threaded connection. An insulating member 960 may be disposed above the substructure 920. An attachment member 970 may be secured to the protrusion 940, such as by engaging the fastening portion 950. In some implementations, the fastening portion 950 and attachment member 970 may have a threaded engagement, although other attachment interfaces may be used. A polymeric membrane 965 overlays the insulating member 960 and may be bonded to the attachment member 970 with a bonding material 980. In some implementations, the bonding material 980 may be a coating of thermoplastic material applied to attachment member 970. In other implementations, a carrier tape and/or an adhesive may be used to couple polymeric membrane 965 to the attachment member 970.

In addition, the described methods and systems can also reduce damage to a polymeric membrane. For example, when objects are unattached but are in contact, debris may become lodged between the object and the polymeric membrane, and, because of the relative movement between the two, the debris may act as an abrasive on the polymeric membrane. Over time, holes, rips, or other damage may occur to the polymeric membrane exposing the underlying structure to the environment, such as moisture, wind, etc. This exposure can cause damage to the structure. However, the present disclosure describes methods and systems that avoid these drawbacks.

Additionally, some of the methods and systems described herein also provide for securing one or more objects to a polymeric membrane without piercing the polymeric membrane. Consequently, objects remain attached to the polymeric membrane without providing a pathway for moisture or other objects, e.g., insects, debris, etc., to pass through the membrane. Again, this can have particular value in waterproofing covering applications where an unperforated covering is greatly desired.

Figure 14:
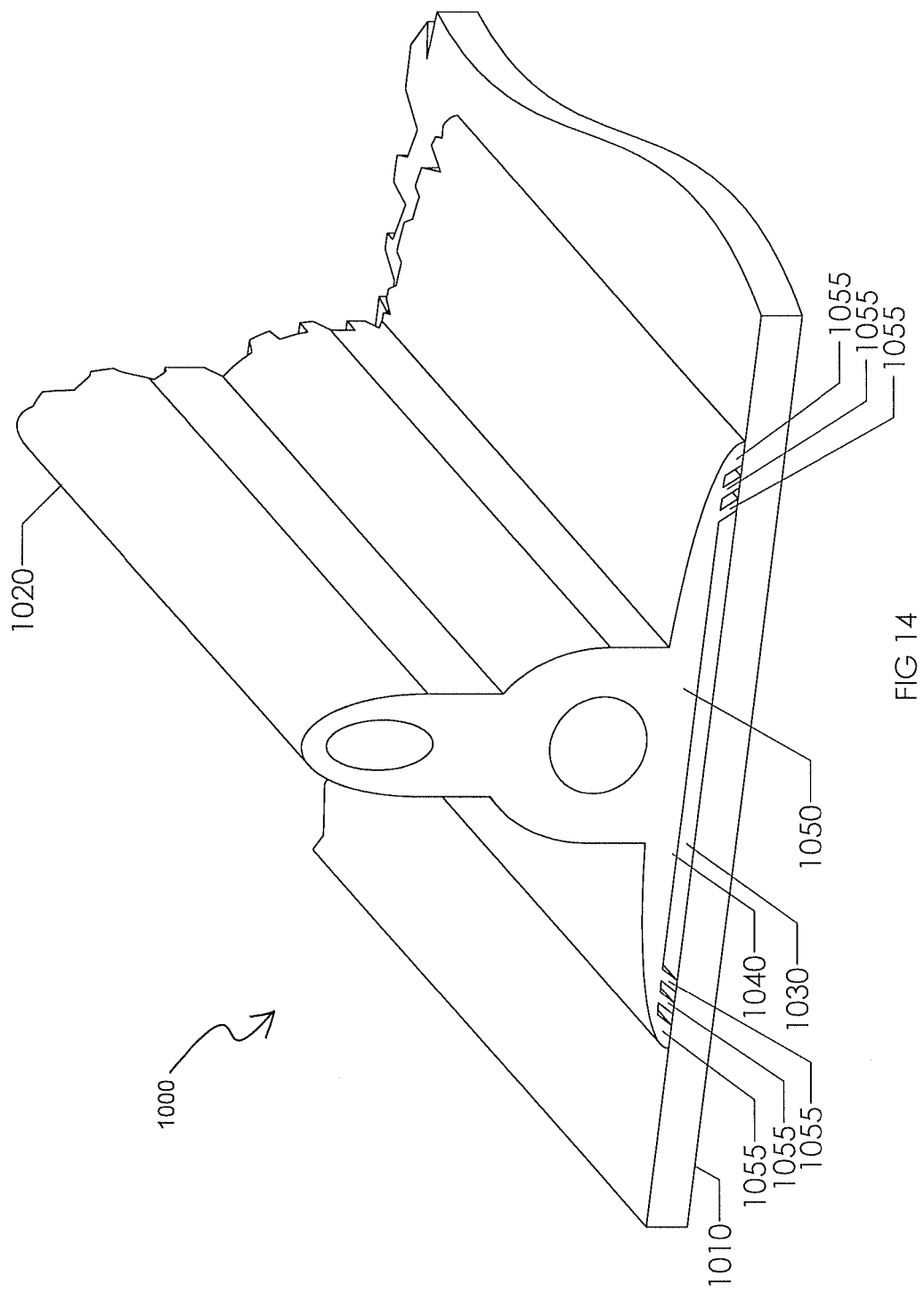
FIG. 14 is an example system for bonding a ridge member to a polymeric membrane.

Another example system 1000 is illustrated in FIG. 14. The system 1000 includes a polymeric membrane 1010, a ridge member 1020, and a bonding member 1030. In some implementations, the polymeric membrane 1010 may form a portion of a roof structure, such as an exterior membrane. The ridge member 1020 may be coupled to the polymeric membrane 1010 by the bonding member 1030. In some instances, the bonding member 1030 may be a double sided carrier tape similar to the carrier tape described above. In some implementations, the adhesive on the sides of the carrier tape may be selected to provide a bond according to the material forming the polymeric membrane 1010 and/or the ridge member 1020. In other implementations, the bonding member 1030 may be an adhesive selected to adhere polymeric membrane 1010 to the ridge member 1020. In some instances, the adhesive may be an adhesive similar to the adhesive described above.

The bonding member 1030 may occupy a channel 1040 formed in a base 1050 of the ridge member 1020. Lips 1055 may also be formed in the ridge member 1020 to aid in preventing intrusion of fluids and other materials into the channel 1040. A benefit of the bonding member 1030 is that while coupling the ridge member 1020 to the polymeric membrane 1010, the bonding member 1030 may have a bonding strength less than the yield strength of the polymeric membrane 1010 and/or the ridge member 1020. Consequently, the bonding member 1030 will yield, separating the ridge member 1020 from the polymeric membrane 1010 when a shearing load on the ridge member 1020 exceeds the strength of the bonding member 1030. Consequently, the bonding member 1030 will yield without damaging either the ridge member 1020 or the polymeric membrane 1010. For example, in an application in which the polymeric membrane 1010 and ridge member 1020 form an exterior portion of a roof structure, a shearing force on the ridge member 1020, for example, caused by a sheet of ice formed on the roof structure, would not tear the polymeric membrane 1010 as the ice sheet moves down a slope of the roof. Rather, the shearing force would merely sever the ridge member 1020 from the polymeric membrane 1010. In other implementations, the bonding member 1030 may have a yield strength equal to or greater than one or more of the ridge member 1020 and/or the polymeric membrane 1010.

Figure 15:
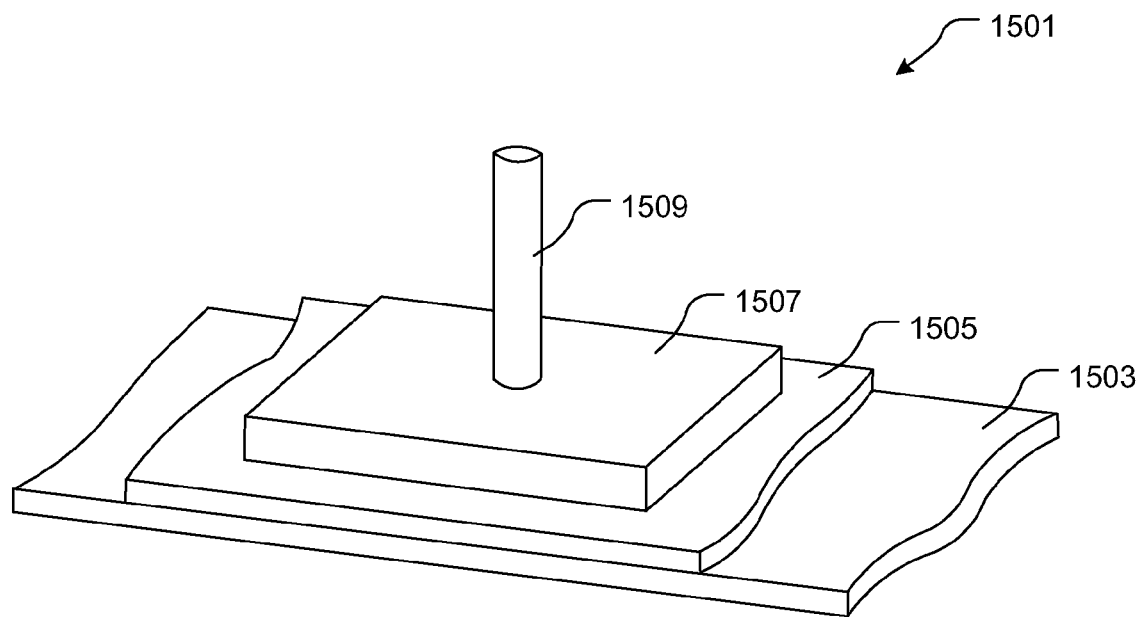
FIG. 15 is an oblique view of a mounting system.
Figure 16:
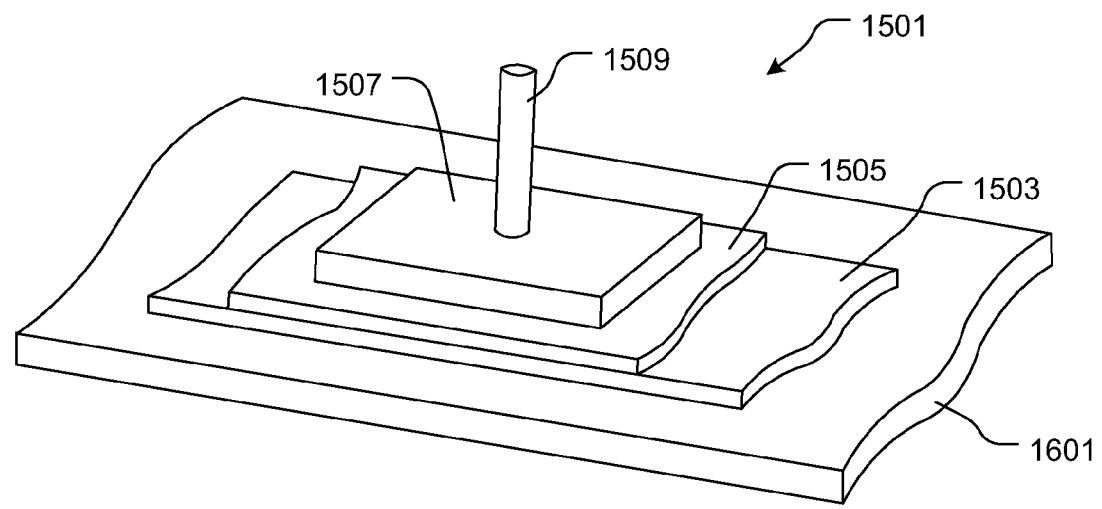
FIG. 16 is an oblique view of a mounting system of FIG. 15 shown attached to a support structure.

Referring now to FIGS. 15 and 16 in the drawings, FIG. 15 shows an oblique view of a mounting system 1501 according to the preferred embodiment of the present invention, while FIG. 16 shows an oblique view of mounting system 1501 attached to a support structure 1601. It should be appreciated that mounting system 1501 is substantially similar in form and function to the mounting systems described above. Like the mounting systems disclosed herein, mounting system 1501 utilizes one or more membranes to securely attach an object to the support structure, which includes, but should not be limited to a polymeric membrane and/or a rooftop. Mounting system 1501 comprises one or more membranes that elastically extend as a force is exerted on the object attached thereto. Further description and illustration of the elastic membrane is provided with reference to FIGS. 17-20C.

Mounting system 1501 comprises one or more of a first membrane 1503, a second membrane 1505, and an object 1507. First membrane 1503 is preferable composed of a polymeric material and is adapted to securely bond with at least a portion of second membrane 1505. It should be understood that first membrane 1503 is an optional membrane. For example, second membrane 1505 could attach directly to the support structure. However, as in most applications, the first membrane is adapted to attach directly to the support structure and the second membrane is adapted to bond to a top surface of the first membrane.

In the preferred embodiment, second membrane 1505 thermally fuses to first membrane 1503; however, it should be appreciated that alternative embodiments could incorporate different methods for bonding second membrane 1505 to first membrane 1503, as disclosed herein and as conventional known in the art. Object 1507 is preferable a mounting plate substantially similar in form and function to the mounting plates disclosed herein; however, it should be understood that object 1507 should not be limited to a mounting plate, but could include other devices in lieu of a mounting plate. For example, in some embodiments, object 1507 could be an attachment device, i.e., a quick-release device, for securing a structure to mounting system 1501. Mounting system 1501 is further provided with an optional protrusion 1509 adapted to attach to object 1507. Protrusion 1509 is substantially similar in form and function to the protrusions disclosed herein, wherein the protrusion is utilized for securing a riser (not shown) to mounting system 1501.

It should be understood that mounting system 1501 could include the additional features of the mounting systems disclosed above. For example, mounting system 1501 could include a third polymeric material, a riser, a bonding medium, and/or other features described herein. Furthermore, the first and second membranes of mounting system 1501 could be composed of the same elastic materials described herein in addition to other suitable materials for providing elasticity to second membrane 1505 and/or any other desired membrane.

Figure 17:
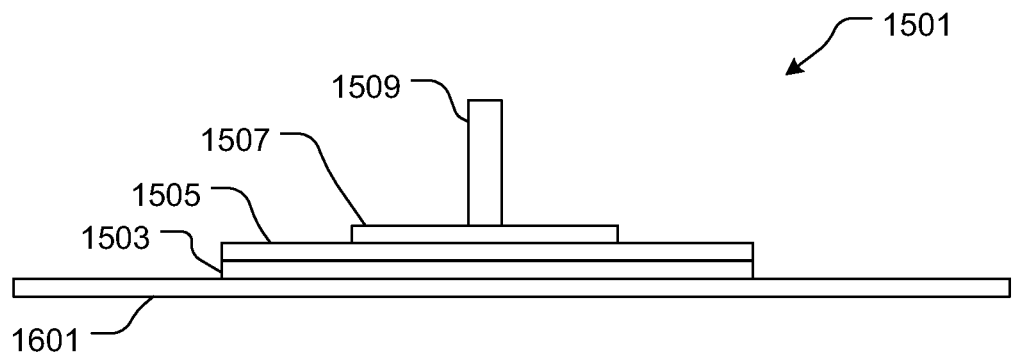
FIG. 17 is a front view of the mounting system of FIG. 15.
Figure 18:
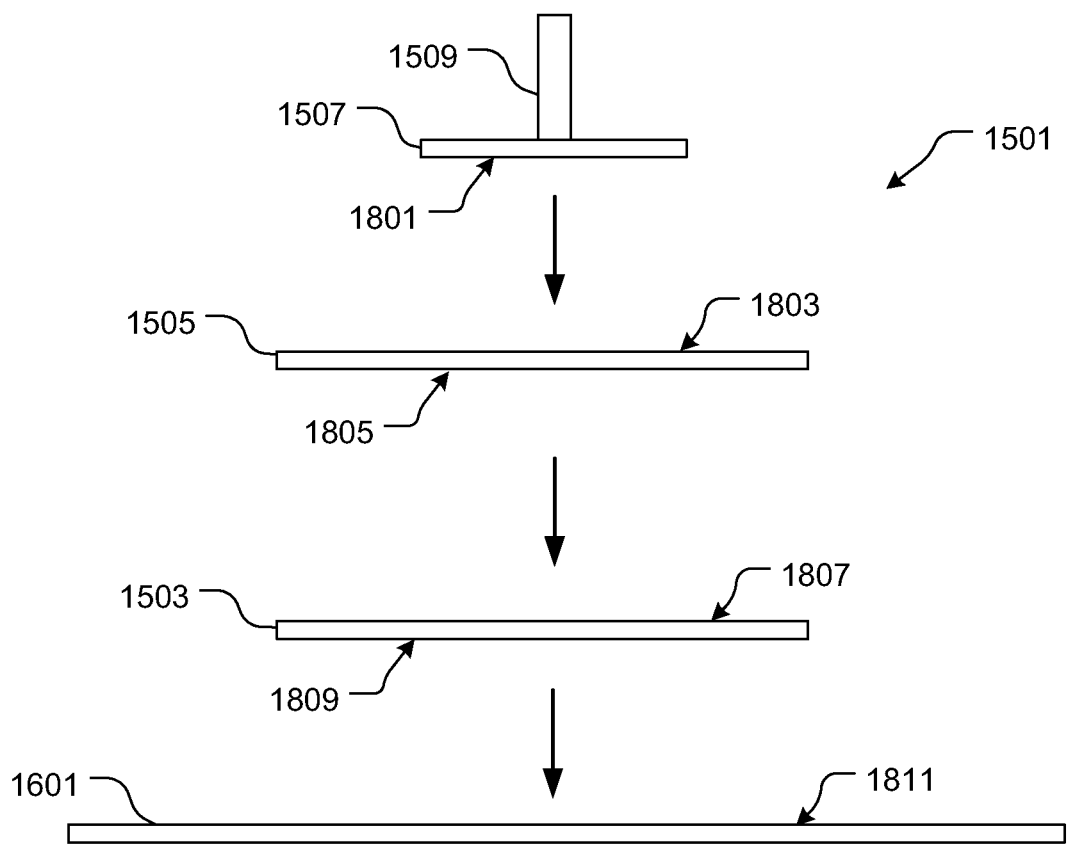
FIG. 18 is an exploded front view of the mounting system of FIG. 15.

Referring now to FIGS. 17 and 18 in the drawings, front views of mounting system 1501 are shown. FIG. 17 shows an assembled mounting system 1501, while FIG. 18 shows and exploded view of mounting system 1501. Object 1507 includes a bottom surface 1801 which bonds to an upper surface 1803 of second membrane 1505. Second membrane includes a lower surface 1805 which bonds to a top surface 1807 of first membrane 1503. First membrane 1503 includes a bottom surface 1809 which attaches to a top surface 1811 of support structure 1601.

Figure 19:
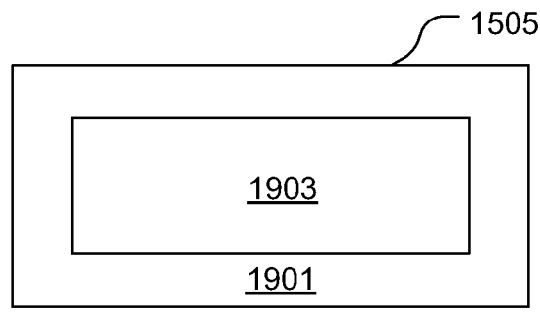
FIG. 19 is a bottom view of a membrane of the mounting system of FIG. 15.

Referring to FIG. 19 in the drawings, a bottom view of second membrane 1505 is shown. Lower surface 1805 preferably comprises two surface areas, a first surface area 1901 being adapted to extend peripherally around a perimeter of lower surface 1805, and a second remaining surface area 1903, which is preferably enclosed within surface area 1901. In the preferred embodiment, area 1901 is bonded to top surface 1807 of first membrane 1503, while area 1903 remains separable from top surface 1807 of first membrane 1503. This feature allows second membrane 1505 to elastically extend in a direction away from first membrane 1503 as a force is exerted on object 1507.

Figure 20A:
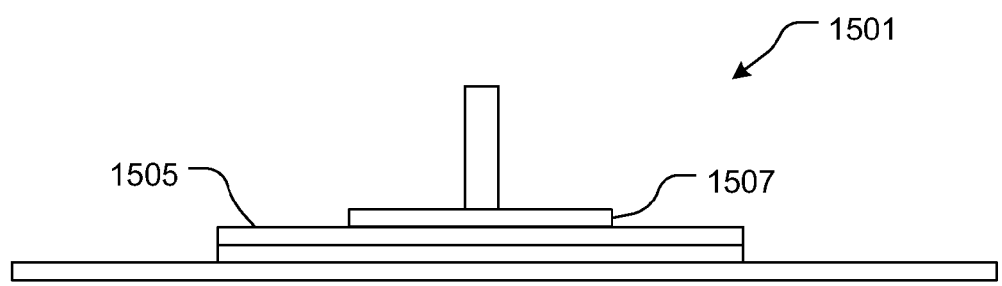
FIGS. 20A-20C are front views of the mounting system of FIG. 15 shown as a force is exerted on an object attached to the mounting system.
Figure 20B:
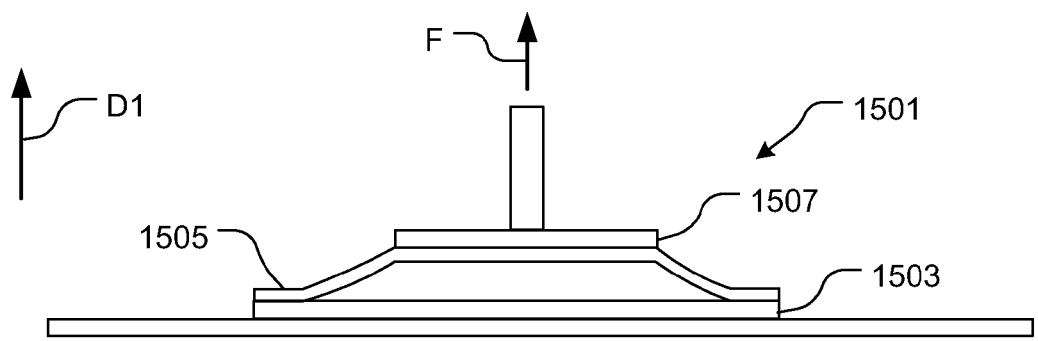
Figure 20C:
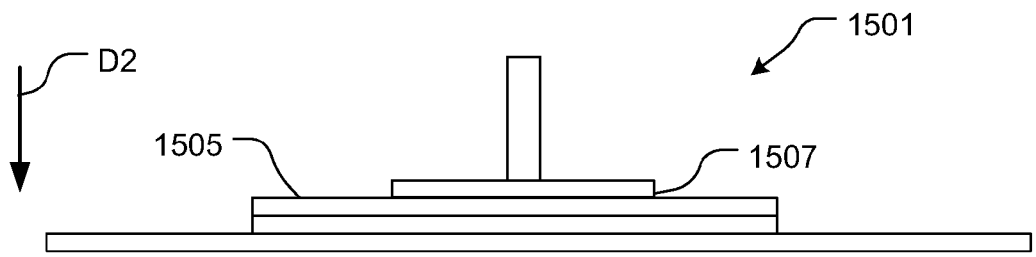

Referring to FIGS. 20A-20C in the drawings, front views of mounting system 1501 are shown. FIGS. 20A-20C depicts second membrane 1505 elastically extending away from support structure 1601. Specifically, as a force F is exerted on object 1507, second membrane 1505 elastically extends in the direction of the force, and then returns to its original position after the force dissipates. FIG. 20A shows mounting system 1501 prior to force exerted against object 1507. FIG. 20B shows second membrane 1505 elastically extending in direction D1 as a force F is exerted on object 1507. FIG. 20C shows second membrane 1505 moving in the direction D2, thus returning back to its original position after force F1 is applied.

Figure 21:
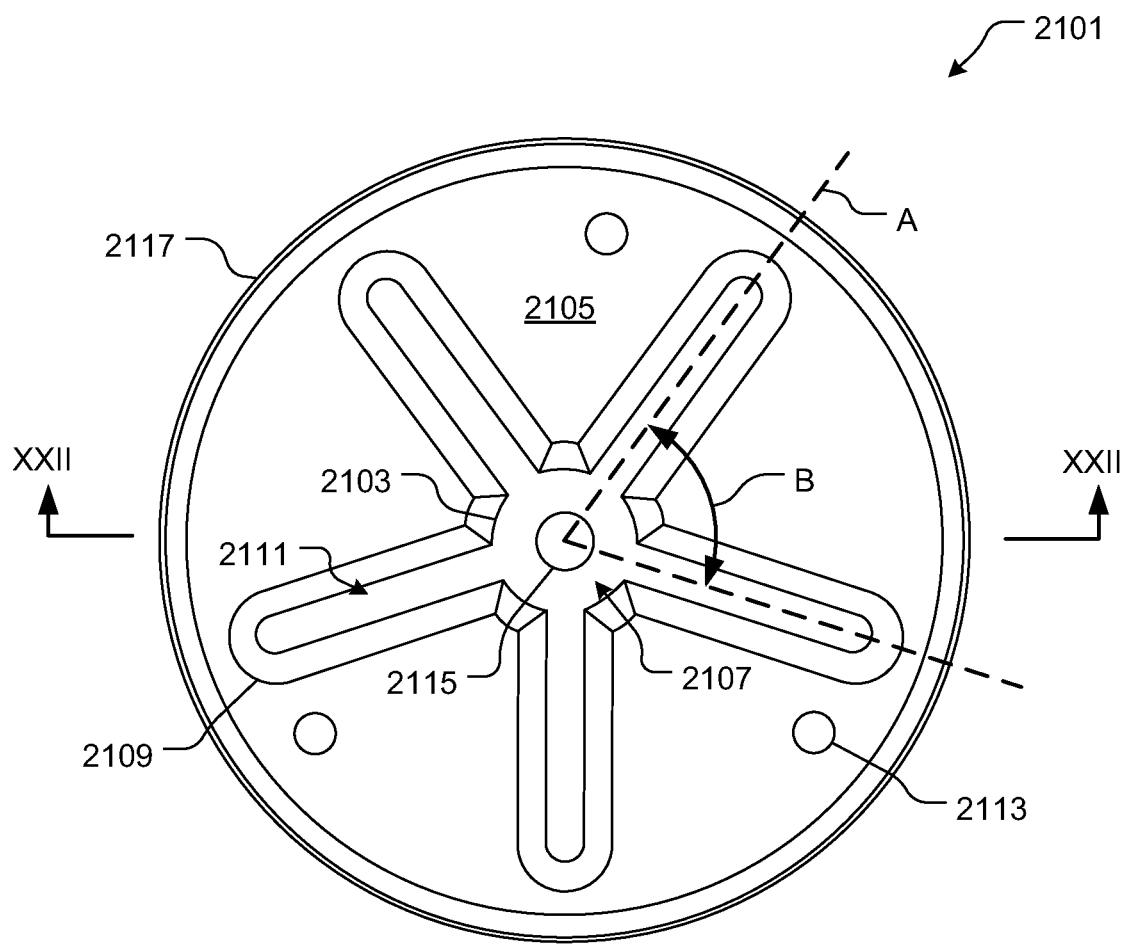
FIG. 21 is a top view of a mounting plate according to the preferred embodiment of the present invention.
Figure 22:
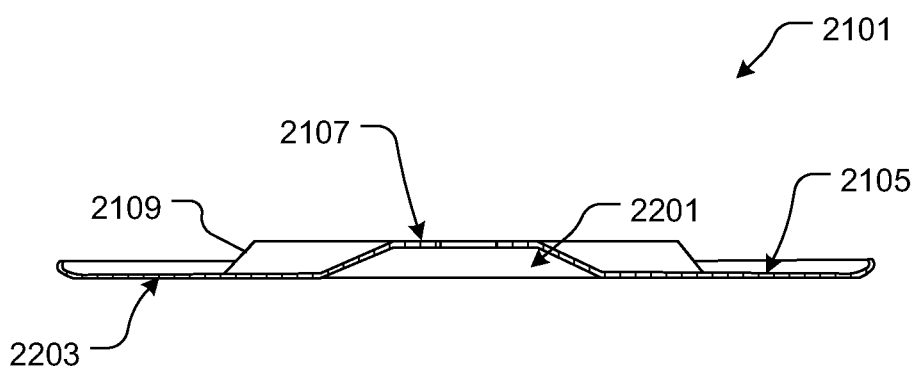
FIG. 22 is a side cross-sectional view of the mounting plate of FIG. 21 taken at XXII-XXII.

Referring now to FIGS. 21 and 22 in the drawings, respective top and side cross-sectional views of a mounting plate 2101 are shown. It should be appreciated that mounting plate 2101 is substantially similar in function to the mounting plates shown and described herein. Specifically, mounting plate 2101 is adapted to secure an object such as a fastener, riser, attachment device, and/or other suitable device to the mounting system.

During assembly, a worker attaches an object, i.e., a solar panel attachment, to the mounting plate, and in some embodiments, it is not feasible to couple the object at a desired position and orientation because the raised surfaces of the mounting plate causes the object to tilt. The mounting plate of the present invention overcomes such problems by extending the contact surface area between the mounted object and the mounting plate, which in turn creates a relatively planar surface area for mounting objects thereto. To do this, mounting plate 2101 is provided with one or more elongated members adapted to extend from a primary housing. The housing and members form a relatively planar surface area for supporting the object resting thereon. Of course, it should be understood that mounting plate 2101 is not intended to be limited to the figures and description below, but could include the features of the mounting plates described herein and other modifications without departing from the spirit thereof.

Mounting plate 2101 comprises a housing 2103 raised from a base 2105, the housing being adapted to receive and support an object, i.e., a riser (not shown) thereon. Housing 2103 preferably forms a cavity 2201 for receiving a bolt, nut, and/or other any other type of fastener. However, it should be appreciated that alternative embodiments could include a solid housing, in lieu of a hollow cavity, and a shaft disposed therein for fastening to the object. Housing 2103 creates a contact surface area 2107, which receives and supports the object attached to mounting plate 2101.

Mounting plate 2101 is provided with one or more elongated members 2109 with a top surface area 2111 having a height relative flush with contact surface area 2107. Members 2109 are adapted to extend the contact surface area between the object and mounting plate 2101, which in turn creates a relatively planar surface area for mounting objects thereto. In the preferred embodiment, housing 2103 and members 2109 form a continuous contact surface area. However, it should be appreciated that alternative embodiments could include members spaced apart from housing 2103. For example, alternative embodiments could include one or more isolated members spaced apart from the housing and adapted to receive and maintain a flush surface area with the housing for mounting an object thereon.

In the preferred embodiment, mounting plate 2101 comprises five elongated members 2109, each member having a longitudinal centerline A, and each longitudinal centerline A being oriented at the same angle B relative to each other on a surface planar to base 2105. It should be appreciated that alternative embodiments could include more less elongated members for supporting the object. For example, alternative embodiments could include three members in lieu and/or different angles relative to each other.

Mounting plate 2101 is further provided with one or more optional holes 2113 for receiving a fastener (not shown) and a hole 2115 extending through the thickness of housing 2103. Hole 2115 is utilized to either receive a attachment device, i.e., a fastener, of the object being attached thereon or adapted to allow a fastener to extend therethrough for fastening to the object. In some embodiments, hole 2115 could be threaded for threadingly engaging with a threaded fastener. Mounting plate 2101 also includes an optional rim 2117 extending peripherally along an edge of base 2105. It should be appreciated that although shown in the circular form, mounting plate 2101 could easily be manufactured in different geometric shapes, depending on the desired application.

Figure 23:
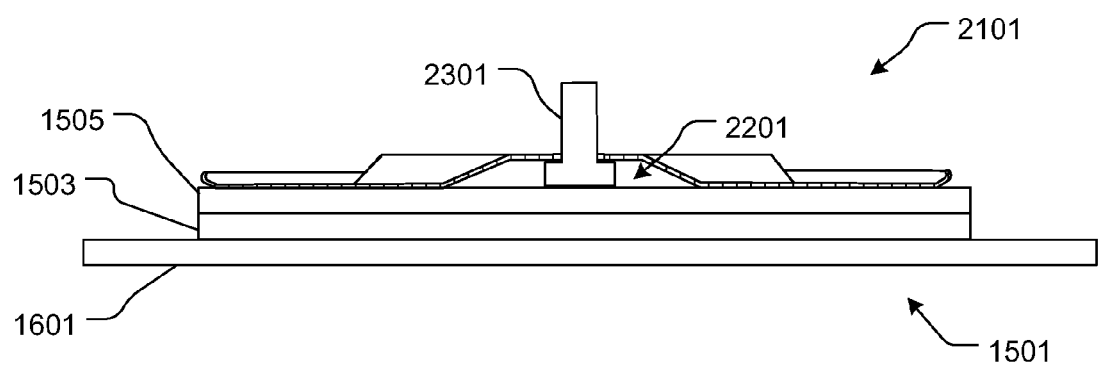
FIG. 23 is a side view of the mounting plate of FIG. 22 shown attached to the mounting system of FIG. 17.

Referring to FIG. 23 in the drawings, a cross-sectional side view of mounting plate 2101 taken at XXII-XXII is shown attached to mounting system 1501. In the preferred embodiment, an adhesive, as described herein, is applied to a bottom surface 2203 of mounting plate 2101 and thereafter bonded, preferably thermally fused, to membrane 1505 of mounting system 1501. In the exemplary embodiment, a fastener 2301 is shown securely positioned within cavity 2201.

Figure 24:
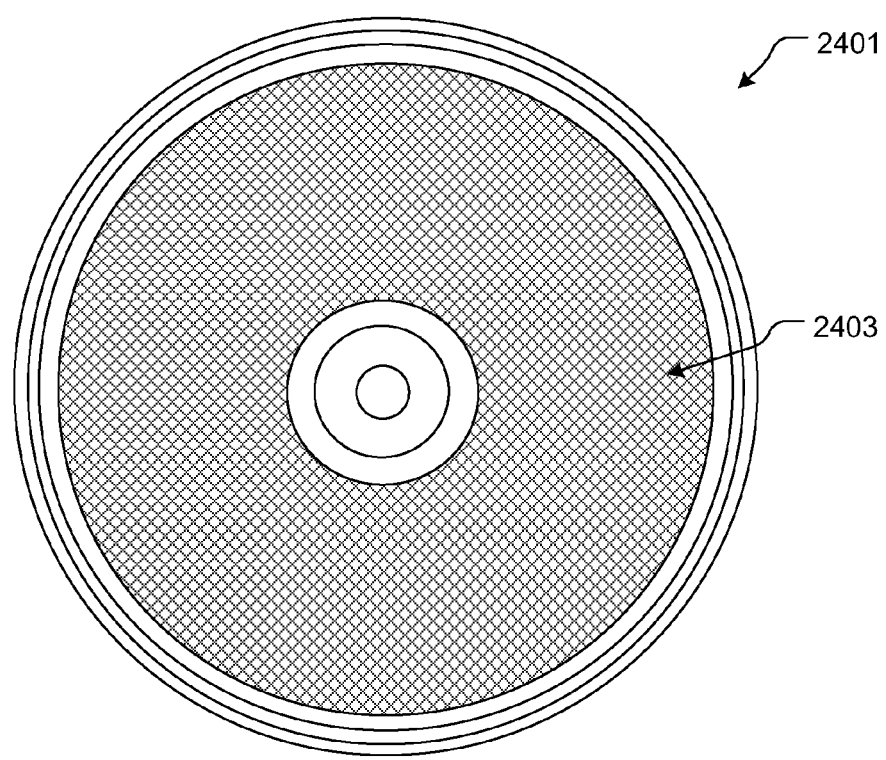
FIG. 24 is a front view of an alternative embodiment of the mounting plate of FIG. 21

Referring now to FIG. 24 in the drawings, a front view of an alternative embodiment of mounting plate 2101 is shown. Mounting plate 2401 is adapted with a perforated surface area 2403. The perforated areas allow the membrane of the mounting system to extend therethrough as heat is applied to the membrane. Thereafter, the membrane securely bonds to above, within, and below the perforated areas after the membrane is cooled.

It should be appreciated that mounting plate 2401 is substantially similar in function to the mounting plates shown and described herein. Specifically, mounting plate 2401 is adapted to secure an object such as a fastener, riser, attachment device, and/or other suitable device to the mounting system. The features of the mounting plates described herein could easily be adapted to include the features of mounting plate 2401, and likewise mounting plate 2401 could be adapted to include the features of the mounting plates described herein. Of course, it should be understood that mounting plate 2401 is not intended to be limited to the embodiment shown in FIG. 24, but includes the features of the mounting plates described herein and other modifications without departing from the spirit thereof.

Figures 25, 26:
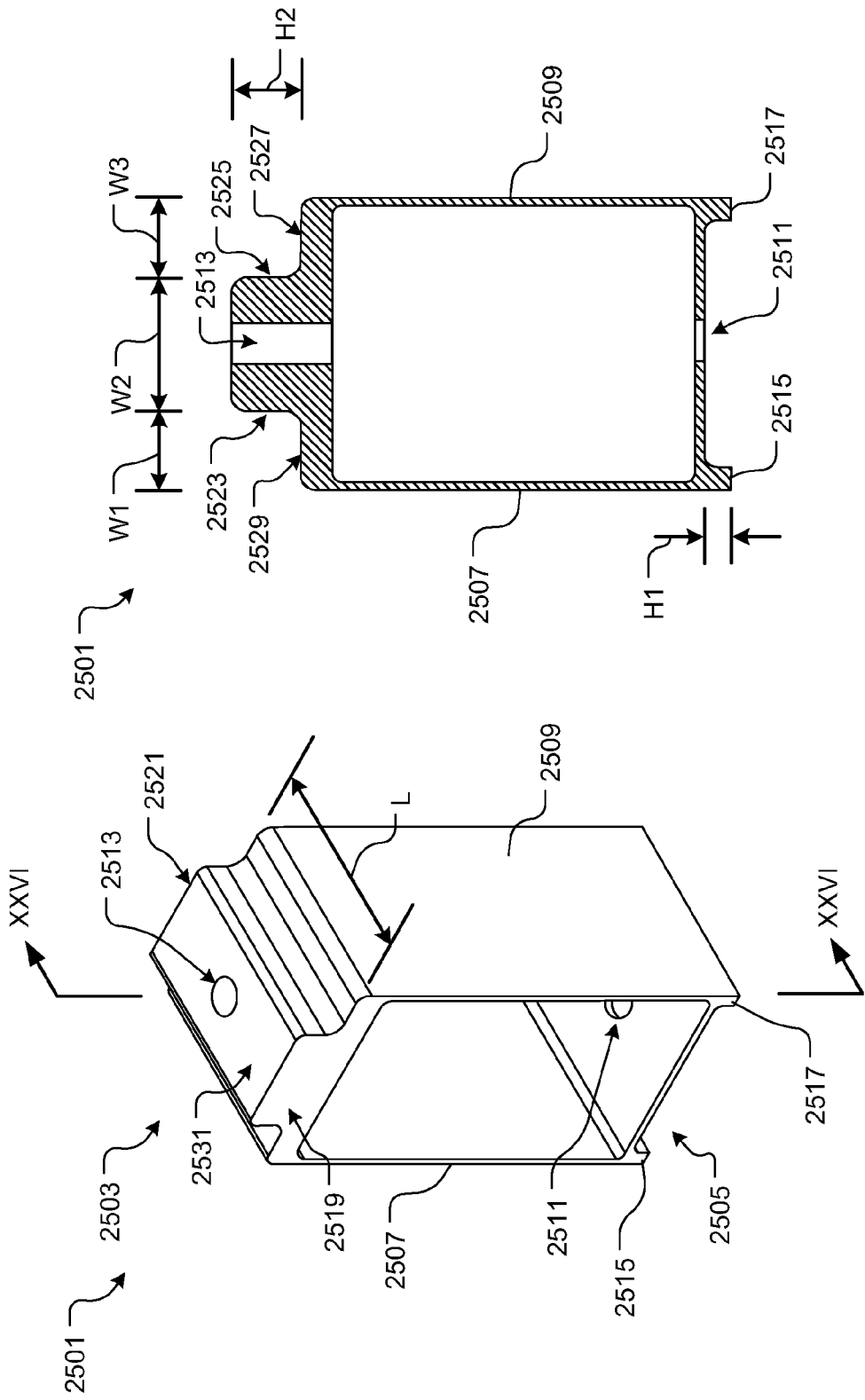
FIG. 25 is an oblique view of a riser according to the preferred embodiment of the present invention.
FIG. 26 is a cross-sectional front view of the riser of FIG. 25 taken at XXVI-XXVI.

Referring now to FIGS. 25 and 26 in the drawings, FIG. 25 shows an oblique view of a riser 2501 according to the preferred embodiment of the present invention, while FIG. 26 shows a front cross-sectional view of riser 2501 taken at XXVI-XXVI of FIG. 25. In the preferred embodiment, riser 2501 is adapted to couple to and elevate an object, i.e., an attachment device for a solar panel, at a desired height, preferably 4 inches, above a structure. It should be understood that, riser 2501, and the alternative embodiments disclosed herein, are adapted to couple to one or more of the mounting systems described herein and/or other modifications without departing from the spirit thereof. In addition, it should be appreciated that riser 2501 and other alternative embodiments thereof could easily be adapted to fasten to other types of devices in lieu of a mounting assembly.

Riser 2501 is preferably composed of a rigid, metallic material such as aluminum, which allows little to no flexure, thus restricting transverse, longitudinal, and rotational movement of riser 2501. The metallic material allows an object, such as a solar panel, to rigidly attach to the structure via riser 2501. However, it should be appreciated that alternative embodiments of riser 2501 could be composed of different materials, both flexible and rigid, depending on the preferred application. For example, riser 2501 could be composed, partially or in whole, of a composite, wood, and/or an elastomeric material, which creates flexibility, conductive resistance, and/or other desired attributes.

Riser 2501 provides significant advantageous over conventional devices for securing an object to a roof structure. Specifically, riser 2501 is preferably manufactured through an extruding process, wherein multiple risers are formed simultaneously as a continuously extruded member. During the manufacturing process, the extruded member is transversely cut to form individual risers. Then, two opposing holes are machined on opposing surfaces of the riser for attaching the riser to both the mounting plate and the object coupled thereto. The relatively simple design and advanced extruding process greatly reduces the manufacturing costs.

Riser 2501 comprises an attachment portion 2503 for securing an object to riser 2501 and a base portion 2505 for coupling riser 2501 to one or more mounting systems described herein. In the exemplary embodiment, riser 2501 is adapted to attach to mounting assembly 110, which in turn attaches to a roof structure. Of course, it should be understood that although described as being utilized with a roof structure, riser 2501 could easily be utilized with other structures in lieu of the preferred roof structure, i.e, a vertical wall, membrane for covering ponds, and/or other suitable structures.

Riser 2501 comprises a first sidewall 2507 and a second sidewall 2509 extending relatively parallel to each other. The sidewalls are adapted to elevate attachment portion 2503 at a predetermined height relative to the structure (not shown). Riser 2501 further comprises a first attachment device 2511, which is preferable a hole extending through the thickness of base 2505 and a second attachment device 2513, which is preferable a hole extending through the thickness of attachment portion 2503. Attachment device 2511 is adapted to couple riser 2501 to the mounting plate, while attachment device 2513 is adapted to couple an object to riser 2501.

Base 2505 preferably includes two elongated leg members, a first leg 2515 and a second leg 2517, both legs being adapted to elevate base 2505 at a height H1 above the top surface of the mounting plate. In the preferred embodiment, leg 2515 and leg 2517 elevate base 2505 above one or more raised surfaces of the mounting plate. For example, the mounting plate, as shown and described above, could include a raised surface directly underneath base 2505, thereby requiring base 2505 to be raised at a height H1 to create a tight, secure fit between riser 2501 and the mounting system. It should be appreciated that leg 2515 and leg 2517 are optional features and are not required in alternative embodiments wherein the mounting plate is devoid of raised surfaces below base 2505. In these alternative embodiments, base 2505 could easily be adapted to sit directly on the top surface of the mounting plate.

Figure 27:
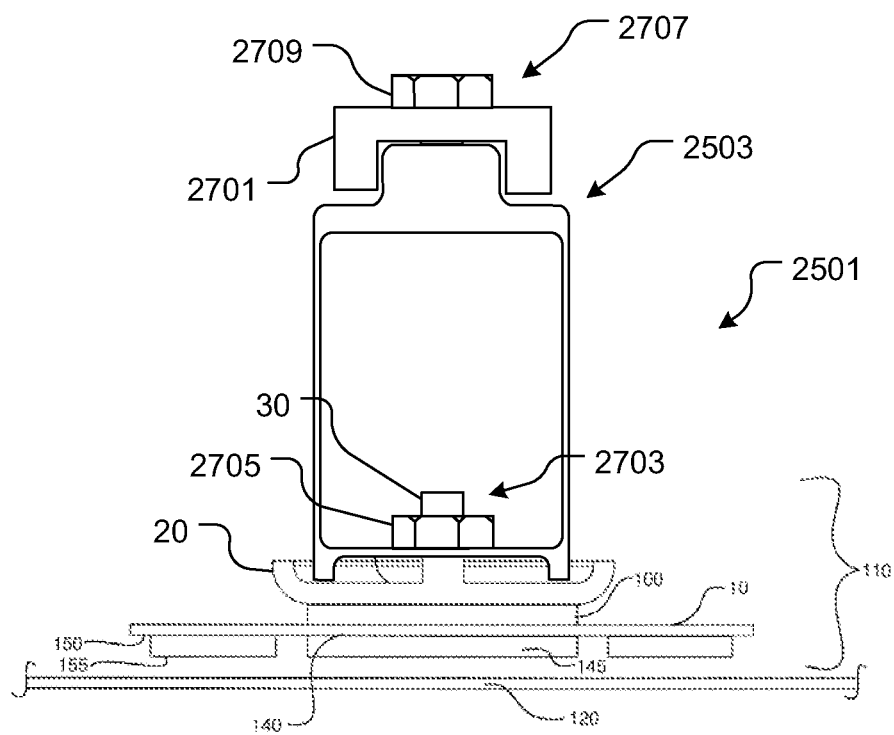
FIG. 27 is a front view of the riser of FIG. 25 shown attached to the mounting assembly of FIG. 4.

Attachment portion 2503 includes one or more surfaces for abutting against the object coupled thereto (see FIG. 27). Attachment portion 2503 preferably comprises six surfaces, a front surface 2519, an opposing rear surface 2521, a side surface 2523, an opposing side surface 2525, a first top surface 2527, a second top surface 2529, and an elevated top surface 2531. In the preferred embodiment, riser 2501 has a length L, a top surface width W1 extending the width of surface 2529, a top surface width W2 extending the width of surface 2531, a top surface width W3 extending the width of surface 2527, and a height H2 extending the height between top surface 2531 and surface 2529. In the preferred embodiment, W2 is greater than W1 or W3 and H2 has a length of approximate ⅜ of an inch. Of course, it should be understood that the foregoing lengths, widths, and heights are not intended to limit riser 2501 to these dimensions. It should be appreciated that alternative embodiments could include different dimensions depending on the desired application.

In the preferred embodiment, an object 2701, like that shown in FIG. 27, rests on top surface 2531 and/or top surfaces 2527 and 2529. Side surfaces 2527 and 2529 and/or front surface 2519 and rear surface 2521 provide means for restricting movement of the object. For example, the object could include a surface extending alongside surface 2523, which creates contact and restricts rotational movement of the object as rotational torque is applied thereto.

Referring now to FIG. 27 in the drawings, a front cross-sectional view of riser 2501 is shown attached to mounting assembly 110 and shown attached to an object 2701. It should be noted that the term mounting assembly and mounting system are interchangeable used herein, and intended to refer to a system adapted to secure an object to a structure. It should also be noted that the front view of mounting assembly 110 is depicted in FIG. 4 above. When assembled, protrusion 30 extends through attachment device 2511, which in turn, is received by an attachment device 2703 for securing base 2505 to assembly 110. In the preferred embodiment, attachment device 2703 is a nut 2705 threadingly engaged with protrusion 30; however, it should be appreciated that alternative embodiments could include different attachment devices, i.e., a quick release device, snap, clip, and/or other suitable devices in lieu of the preferred embodiment.

Attachment device 2511 is preferable a non-threaded hole, which allows the protrusion to slide therein, while attachment device 2513 is preferably a threaded hole, which provides attachment means for a threaded bolt and/or other suitable device. It should be appreciated that alternative embodiments could include either threaded or non-threaded holes in lieu of the preferred embodiment.

During assembly, riser 2501 is positioned on plate 20 such that hole 2511 receives protrusion 30. Thereafter, riser 2501 is attached to plate 20 with attachment device 2703 such that the legs of riser 2501 securely contact the top surface of plate 20. Finally, object 2701 is placed on attachment portion 2503 and secured with attachment device 2707, i.e, a bolt 2709.

Referring now to FIGS. 28 and 29 in the drawings, FIG. 28 shows an oblique view of a riser 2801 according to an alternative embodiment of the present invention, while FIG. 29 shows a front cross-sectional view of riser 2801 taken at XXIX-XXIX of FIG. 28. It should be noted that riser 2801 is substantially similar in function to riser 2501, wherein both riser 2801 and riser 2501 are adapted to elevate an object at a predetermined height above a structure and both risers are adapted to securely attach to a mounting assembly. The features of riser 2801 could easily be incorporated in riser 2501, and likewise, the features of riser 2501 could be incorporated in riser 2801.

Riser 2801 comprises an attachment portion 2803 for securing an object to riser 2801 and a base portion 2805 for attaching riser 2801 to a mounting assembly. Base portion 2805 is preferably a separate member rigidly attached to attachment portion 2803 through bonding means, i.e., welding, to form a unitary body with attachment portion 2803. However, it should be appreciated that attachment portion 2803 and base 2805 could easily be manufactured as a single member in alternative embodiments. For example, riser 2801 could be manufactured through a lathing or milling process.

In the exemplary embodiment, riser 2801 attaches to mounting assembly 110. Of course, it should be understood that riser 2801 could easily be attached to other types of mounting assemblies, either attached to a roof structure or other types of structures.

Riser 2801 comprises a first attachment device 2807, which is preferably a hole, and a second attachment device, which is preferable a hole, both holes being adapted to extend partially through the thickness of attachment portion and base portion, respectively. Attachment device 2811 is adapted to couple riser 2801 to mounting assembly 110, while attachment device 2807 is adapted to secure an object to riser 2801. It should be appreciated that alternative embodiments could include a continuous conduit interconnecting the two opposing attachment devices in lieu of the preferred embodiment. In the preferred embodiment, attachment device 2811 threadingly engages with protrusion 30 of mounting assembly 110, and attachment device 2807 threadingly engages with a threaded bolt and/or other suitable attachment device.

During assembly, riser 2801 is positioned on plate 20 such that attachment device 2811 receives protrusion 30. Thereafter, a worker rotates riser 2801, which in turn, causes attachment device 2811 to threadingly engage with protrusion 30. Finally, an object is placed on surface 2809 and secured with an attachment device (not shown), i.e., a fastener adapted to engage with attachment device 2807.

Riser 2801 is further provided with a cavity 2815 for receiving a raised surface of the mounting plate. It should be appreciated that cavity 2815 is an optional feature and is not required in alternative embodiments where the mounting plate is devoid of raised surfaces directly beneath surface 2813. In these alternative embodiments, base 2805 could easily be adapted to sit directly on the top surface of the mounting plate.

Figure 31:
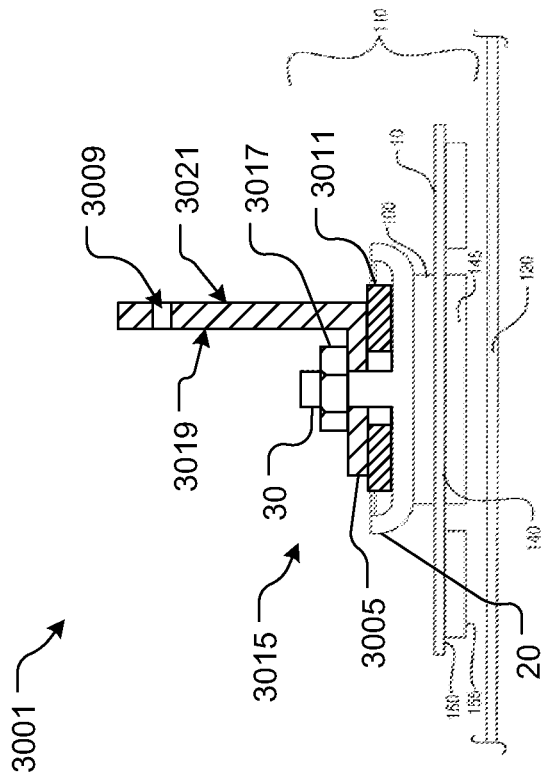
FIG. 31 is a cross-sectional side view of the riser of FIG. 30 taken at XXXI-XXXI.
Figure 30:
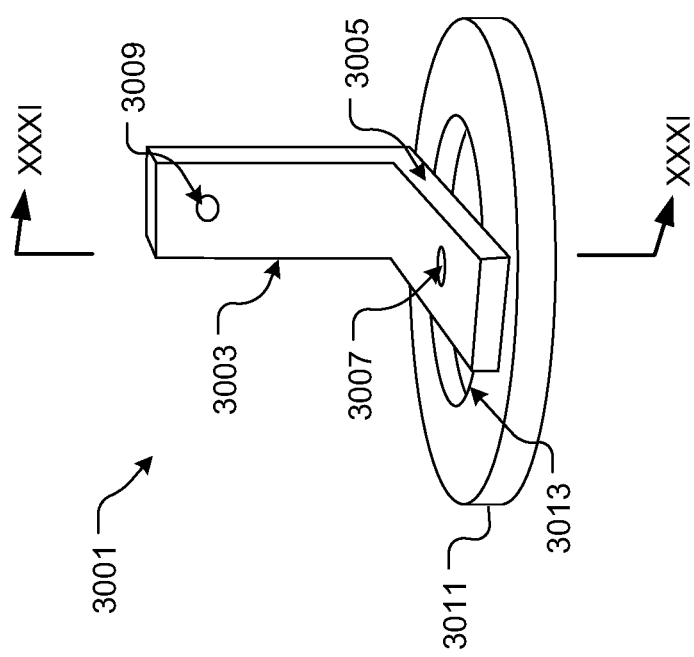
FIG. 30 is an oblique view of a riser according to an alternative embodiment of the present invention.

Referring now to FIGS. 30 and 31 in the drawings, FIG. 30 shows an oblique view of a riser 3001 according to an alternative embodiment of the present application, while FIG. 31 shows a front cross-sectional view of riser 3001 taken at XXXI-XXXI of FIG. 30. FIG. 31 also shows riser 3001 coupled to mounting assembly 110, as depicted in FIG. 4 above. It should be appreciated that riser 3001 is substantially similar in function to riser 2801 and riser 2501, wherein riser 2801, riser 2501 and riser 3001 are adapted to raise an object at a predetermined height above a structure and adapted to securely attach to a mounting assembly. The features of riser 3001 could easily be incorporated in both risers 2501 and 2801, and likewise, the features of risers 2501 and 2801 could be incorporated in riser 3001.

Like risers 2501 and 2801, riser 3001 comprises an attachment portion 3003 for securing an object to riser 3001 and a base 3005 for attaching riser 3001 to a mounting assembly. In the preferred embodiment, riser 3001 is formed as a single member, preferably manufactured through the extruding process described above. Riser 3001 is provided with a first attachment device 3007, which is preferable a hole extending through the thickness of attachment portion 3003 and a second attachment device 3009, which is preferably a hole extending through the thickness of base 3005. Attachment device 3007 provides means for attaching riser 3001 to the roof structure, while attachment device 3009 provides means for securing an object to riser 3001.

Riser 3001 is further provided with a structure 3011, which can either be separable from or rigidly attached to base 3005 through a bonding process, i.e., welding, to form a unitary body with base portion 3005. Structure 3011 elevates base 3005 above a raised surface area (not shown) of the mounting plate. Structure 3011 is provided with a cavity 3013 extending through the thickness of structure 3011 for receiving the raised surface and for allowing protrusion 30 to extend therethrough.

During assembly, riser 3001 is positioned on plate 20 such that hole 3013 and hole 3007 receive protrusion 30. Thereafter, an attachment device 3015, i.e., a bolt 2117, attaches to protrusion 30 for securing riser 3001 to mounting assembly 110. Finally, an object is coupled to either a surface 2019 and/or a surface 2021 of attachment portion 3003 and secured with an attachment device (not shown) adapted to couple to hole 3009.

Figure 32:
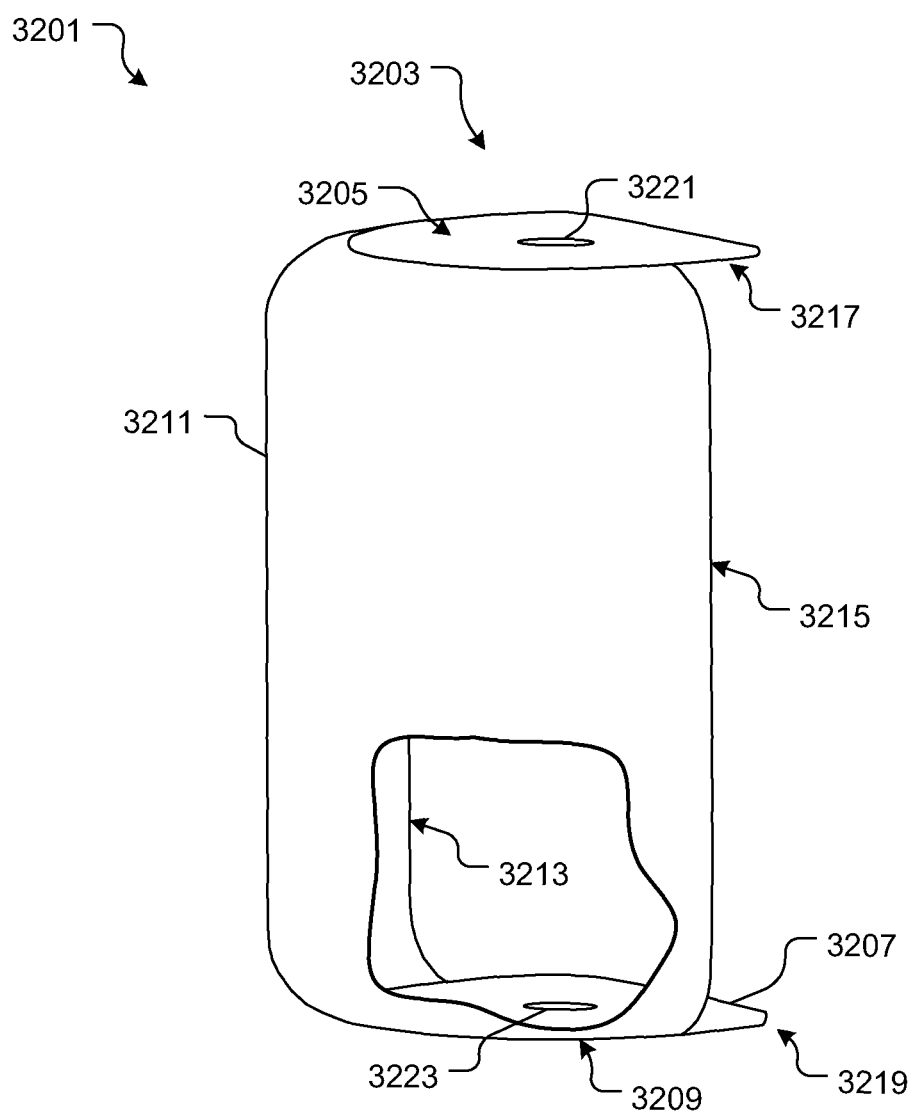
FIG. 32 is an oblique view of a riser according to an alternative embodiment of the present invention.

Referring now to FIG. 32 in the drawings, an oblique view of an alternative embodiment of riser 2501 is shown. Riser 3201 is substantially similar in function to the risers described herein. Specifically, riser 3201 is adapted to elevate an object at a predetermined height above a structure via one or more of the mounting systems described herein. The features of riser 3201 could easily be incorporated in the risers described herein, and likewise the features of risers disclosed herein could be incorporated in riser 3201.

Riser 3201 comprises one or more of an attachment portion 3203 having a top surface 3205 and an opposing base portion 3207 having a bottom surface 3209. Attachment portion 3203 is adapted to support and attach to an object thereon, while base portion 3207 is adapted to secure riser 3201 to one or more of the mounting systems described herein.

Riser 3201 further comprises a sidewall 3211 rigidly attached to attachment portion 3203 and base portion 3209. Sidewall 3211 elevates attachment portion 3203 at a predetermined height, preferably around 4 inches above a structure the mounting system is attached thereto. In the preferred embodiment, sidewall 3211 is manufactured in a curved profile, which is formed through a stamping manufacturing process. It should be appreciated that other profiles, i.e., rectangular profiles, could be utilized in lieu of the preferred embodiment. The curved profile provides sufficient rigidity for supporting the object coupled to attachment portion 3203. In the preferred embodiment, riser 3201 is manufactured with a stamping process; however, it should be appreciated that alternative manufacturing process, i.e., milling, could be utilized in lieu of the preferred process.

Sidewall 3211 curves from a first end 3213 to a second end 3215. In the preferred embodiment, sidewall 3211 does not attach to the entire edged surfaces of attachment portion 3203 and base portion 3207. Attachment portion 3203 includes a top tab portion 3217, while base portion 3207 includes a bottom tab portion 3219. However, it should be appreciated that alternative embodiments could include a sidewall that attach to the entire edged surfaces of the top and bottom members.

Riser 3201 further comprises a first attachment device 3221, which is preferable a hole extending through the thickness of attachment portion 3203 and a second attachment device 3233 extending through the thickness of base portion 3207. In the preferred embodiment, attachment portion 3221 is adapted to couple to the object being mounted thereto, and attachment portion 3223 is adapted to couple riser 3201 to one or more of the mounting systems described herein. It should be appreciated that attachment device 3221 and/or attachment device 3223 could either be threaded or unthreaded, depending on the preferred application.

Figure 33:
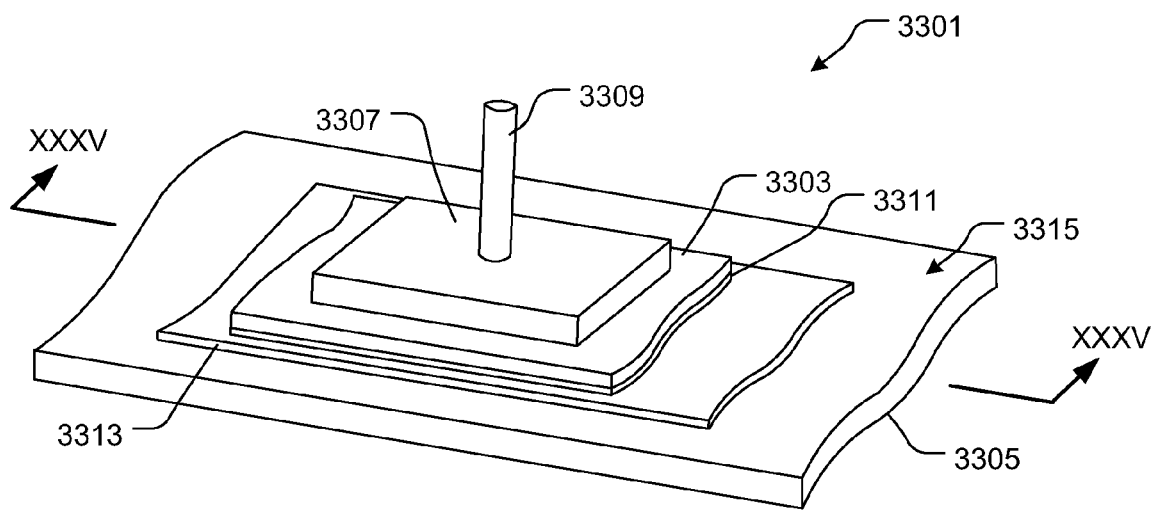
FIG. 33 is an oblique view of an alternative embodiment of the mounting system of FIG. 15.

Referring now to FIG. 33 in the drawings, an alternative embodiment of mounting system 1501 is shown. Mounting system 3301 is substantially similar in form and function to the mounting systems described herein. In particular, mounting system 3301 utilizes one or more elastic membranes to securely attach an object to the support structure, which includes, but should not be limited to a polymeric membrane and/or a rooftop. Of course, it should be understood that mounting system 3301 is not intended to be limited to the figures and description below, but could include the features of the mounting system described herein and other modifications without departing from the spirit thereof, and likewise the mounting systems described herein could incorporate the features of mounting system 3701.

Mounting system 3301 comprises an elastic membrane 3303 bonded to both a structure 3305 and an object 3307. Elastic membrane 3303 is substantially similar in form and function to membrane 1505 described above, namely, elastic membrane 3303 is adapted to elastically stretch in a direction from structure 3305 as a force is exerted on object 3307. An optional protrusion 3309 couples to object 3307, which in turn attaches to a riser (not shown) and/or other structure associated with mounting system 3301.

Figure 35:
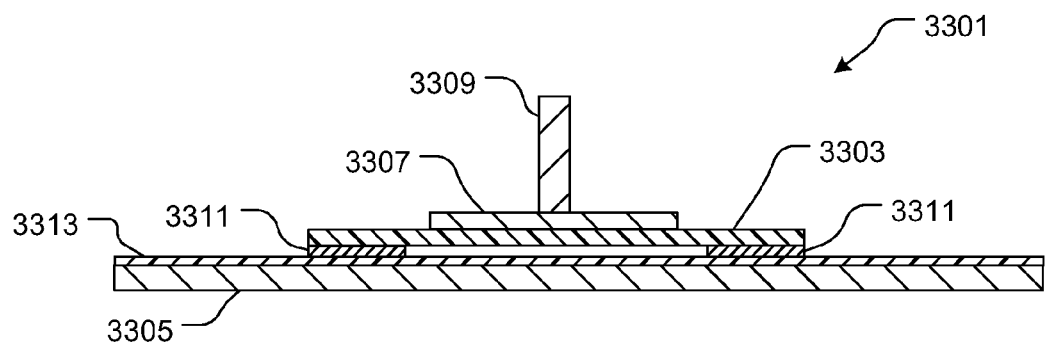
FIG. 35 is a cross-sectional front view of the mounting system of FIG. 33 taken at XXXV-XXXV.

Mounting system 3301 is further provided with a material 3311 preferably thermally fused to a lower surface 3601 of membrane 3303 (see FIG. 35). During assembly, an adhesive 3313 is applied to a top surface 3315 of structure 3305, and then membrane 3303 and material 3311 are placed on at least a portion of adhesive 3313. In the preferred embodiment, adhesive 3313 has a temperature sufficient to thermally bond with material 3311. Material 3311 is preferably composed of a non-woven absorbent polyester material; however, it should be appreciated that alternative embodiments could include other types of materials adapted to form a bond with adhesive 3313. Also, adhesive 3313 is preferably composed of an asphalt material, which is heated to form a bond with material 3311; however, it should be appreciated that alternative embodiments could include other forms of adhesive materials adapted to bond with material 3311.

Figure 34:
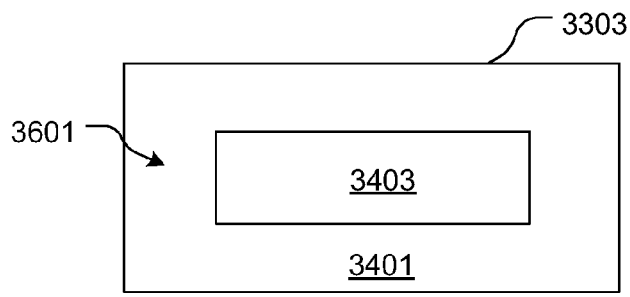
FIG. 34 is a bottom view of a membrane of the mounting system of FIG. 33.

Referring now to FIG. 34 in the drawings, a bottom view of membrane 3303 is shown. Lower surface 3601 preferably comprises two surface areas, a first surface area 3401 extending peripherally around a perimeter of lower surface 3601, and a second remaining surface area 3403, which is preferably enclosed within surface area 3401. In the preferred embodiment, material 3311 is bonded to surface area 3401, and forms a bond with adhesive 3313 applied to top surface 3315 of structure 3305, while area 3403 remains separable from top surface 3315 of structure 3305 such that area 3403 allows membrane 3303 to elastically extend in a direction away from structure 3305 as a force is exerted on object 3307 (see FIG. 20B). Further illustration of material 3311 is shown in at least FIG. 35, wherein a front cross-sectional view clearly shows material 3311 being partially applied to lower surface 3601 and surface area 3403 being separable from structure 3305.

Figure 36:
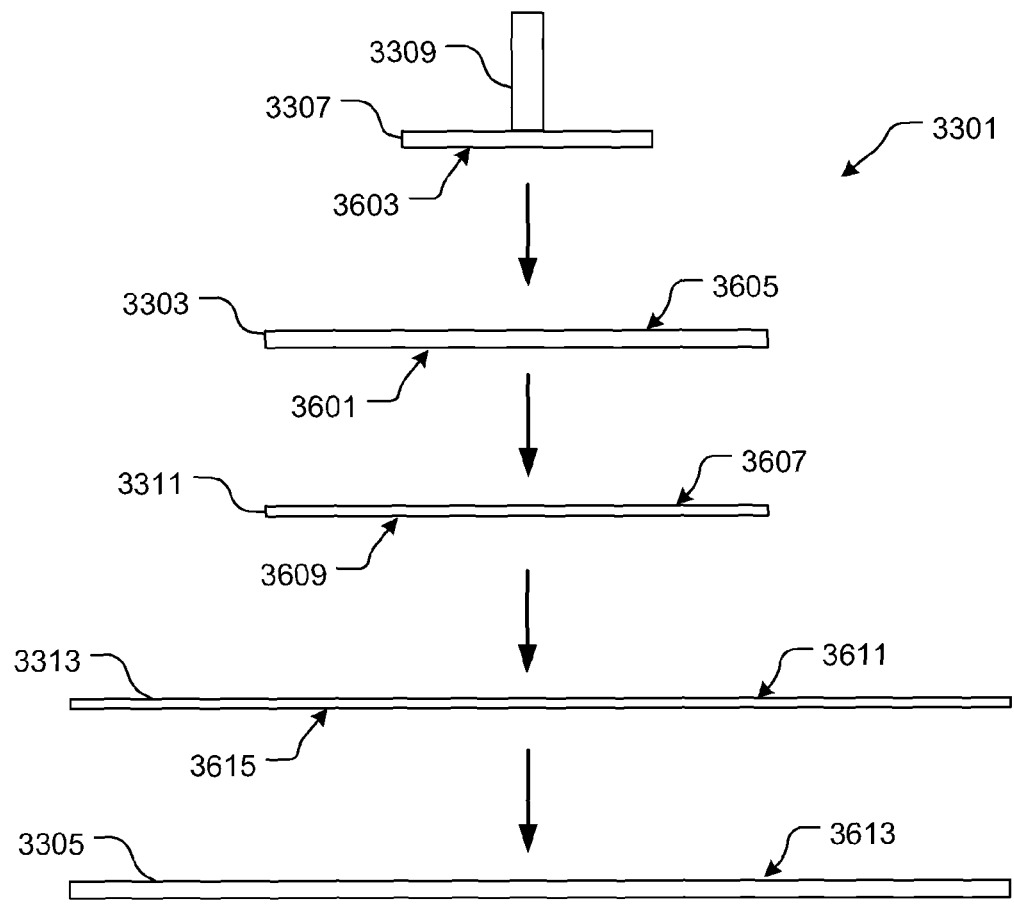
FIG. 36 is an exploded front view of the mounting system of FIG. 33.

Referring now to FIG. 36 in the drawings, an exploded front view of mounting system 3301 is shown. Object 1507 includes a bottom surface 3603 which bonds to an upper surface 3605 of membrane 3303. Membrane 3303 includes lower surface 3601 which bonds to a top surface 3607 of material 3311. Material 3311 includes a bottom surface 3609 which bonds to a top surface 3611 of adhesive 3313. Structure 3305 includes a top surface 3613 which bonds to a bottom surface 3615 of material 3303.

Figure 37:
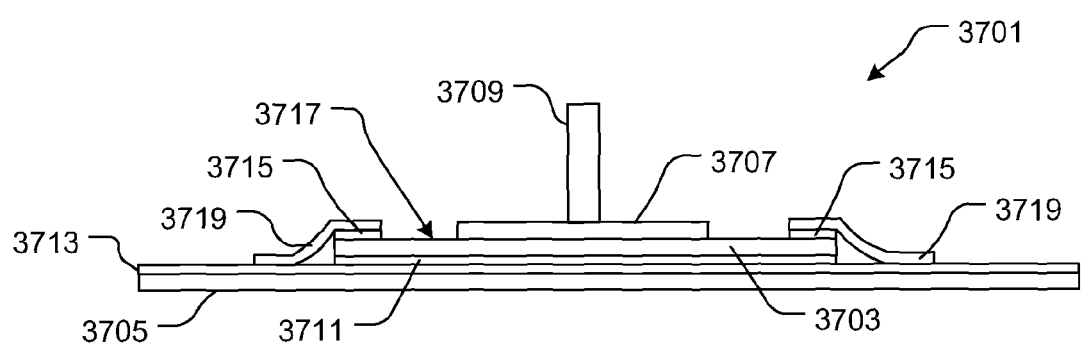
FIG. 37 is an alternative embodiment of the mounting system of FIG. 33.

Referring now to FIG. 37 in the drawings, a front view of an alternative embodiment of mounting system 3301 is shown. Mounting system 3701 is substantially similar in form and function to the mounting systems described herein. In particular, mounting system 3701 utilizes one or more elastic membranes to securely attach an object to the support structure, which includes, but should not be limited to a polymeric membrane and/or a rooftop. Of course, it should be understood that mounting system 3701 is not intended to be limited to the figures and description below, but could include the features of the mounting system described herein and other modifications without departing from the spirit thereof. It should also be appreciated that mounting system 3701 could include the features of the mounting systems described herein, and likewise the mounting systems described herein could incorporate the features of mounting system 3701.

Mounting system 3701 comprises an elastic membrane 3703 bonded to both a structure 3705 and an object 3707. Elastic membrane 3703 is substantially similar in form and function to membrane 3303 described above, namely, elastic membrane 3703 is adapted to elastically stretch in a direction away from the support structure as a force is exerted on object 3707. An optional protrusion 3709 couples to object 3307, which in turn attaches to a riser (not shown) and/or other structure associated with mounting system 3701.

Mounting system 3701 is provided with a material 3711, which attaches to a lower surface of membrane 3703. During assembly, an adhesive 3713 is applied to a top surface of structure 3705, and then membrane 3703 and material 3711 are placed on adhesive 3713, which in turn forms a bond between material 3711 and adhesive 3713.

Mounting system 3701 is further provided with a material 3715 bonded to an upper surface 3717 of membrane 3703. A second bonding adhesive 3719 is applied over at least a portion of material 3715 and applied over at least a portion of adhesive 3713. Material 3715 and adhesive 3719 are adapted to further secure membrane 3703 to structure 3705.

In the preferred embodiment, both material 3711 and material 3715 are composed of a non-woven absorbent polyester material; however, it should be appreciated that alternative embodiments could include other types of absorbent materials adapted to form a bond with adhesive 3713 and/or adhesive 3719. In the preferred embodiment, both adhesive 3719 and adhesive 3719 are composed of a hot asphalt material; however, alternative embodiments could include other forms of adhesive materials adapted to bond with material 3711 and material 3715.

The particular embodiments disclosed above are illustrative only, as the invention may be modified and practiced in different but equivalent manners apparent to those skilled in the art having the benefit of the teachings herein. It is therefore evident that the particular embodiments disclosed above may be altered or modified, and all such variations are considered within the scope and spirit of the invention. Accordingly, the protection sought herein is as set forth in the description. It is apparent that an invention with significant advantages has been described and illustrated. Although the present invention is shown in a limited number of forms, it is not limited to just these forms, but is amenable to various changes and modifications without departing from the spirit thereof.

What is claimed is:

1. A method to mount an object to a support structure, the method comprising:
    elastically moving the object relative to the support structure with an elastic membrane as force is exerted on the object, the elastic membrane comprising:
    an upper surface; and
    a lower surface having:
        a first surface area, the first surface area extending peripherally along at least a portion of a perimeter of the lower surface; and
        a second surface area, the second surface area being at least partially enclosed within the first surface area;
    bonding an absorbent material to the first surface area;
    applying an adhesive to a top surface area of the support structure;
    bonding the absorbent material with at least a portion of the adhesive; and
    wherein the second surface area is positioned at least partially below the object; and
    wherein the first surface area of the elastic membrane remains attached to the support structure via the absorbent material while the second surface area of the elastic membrane remains separable from the support structure such that the second surface area elastically extends in a direction away from the support structure as a force is exerted against the object.

2. The method of claim 1, further comprising:
    attaching a protrusion to the object; and
    extending the protrusion in a direction away from the support structure.

3. The method of claim 1, further comprising:
    coupling a riser to the protrusion;
    wherein the riser extends in a direction away from the support structure.

* * * * *